(12) United States Patent
Garvey et al.

(10) Patent No.: US 8,943,892 B2
(45) Date of Patent: Feb. 3, 2015

(54) AUTOMATED INSPECTION OF SPAR WEB IN HOLLOW MONOLITHIC STRUCTURE

(75) Inventors: Jeffry J. Garvey, Burien, WA (US);
James C. Kennedy, Renton, WA (US);
James J. Troy, Issaquah, WA (US)

(73) Assignee: The Boeing Company, Chicago, IL (US)

( * ) Notice: Subject to any disclaimer, the term of this patent is extended or adjusted under 35 U.S.C. 154(b) by 400 days.

(21) Appl. No.: 13/470,125

(22) Filed: May 11, 2012

(65) Prior Publication Data
US 2013/0304251 A1 Nov. 14, 2013

(51) Int. Cl.
G01N 29/04 (2006.01)
B66F 7/00 (2006.01)
F16M 11/04 (2006.01)
G06F 7/14 (2006.01)

(52) U.S. Cl.
USPC .................. 73/620; 73/618; 702/56; 700/213

(58) Field of Classification Search
USPC .................. 73/620, 618; 702/56; 700/213
See application file for complete search history.

(56) References Cited

U.S. PATENT DOCUMENTS

| | | | |
|---|---|---|---|
| 5,174,325 A | 12/1992 | Okel et al. | |
| 6,722,202 B1 | 4/2004 | Kennedy et al. | |
| 6,993,971 B2 | 2/2006 | Bossi et al. | |
| 7,231,826 B2 | 6/2007 | Bossi et al. | |
| 7,249,512 B2 | 7/2007 | Kennedy et al. | |
| 7,263,889 B2 | 9/2007 | Kennedy et al. | |
| 7,484,413 B2 | 2/2009 | Georgeson et al. | |
| 7,574,502 B2 * | 8/2009 | Clymer et al. | 709/224 |
| 7,726,256 B1 | 6/2010 | Weisenberg | |
| 8,713,998 B2 * | 5/2014 | Troy et al. | 73/104 |
| 2006/0222138 A1 | 10/2006 | Shimamura et al. | |
| 2007/0006657 A1 | 1/2007 | Kennedy et al. | |
| 2010/0095775 A1 | 4/2010 | Sarr et al. | |
| 2013/0250719 A1 * | 9/2013 | Kollgaard et al. | 367/7 |
| 2014/0200832 A1 * | 7/2014 | Troy et al. | 702/38 |

OTHER PUBLICATIONS

U.S. Appl. No. 12/966,268, filed Dec. 13, 2010, entitled "Device and Method for Inspecting a Corner Radius."
U.S. Appl. No. 13/313,267, filed Dec. 7, 2011, entitled "Adaptive Magnetic Coupling System."
Extended European Search Report dated Aug. 14, 2014, European Patent Application No. 13167345.1 (European counterpart of the instant patent application).

* cited by examiner

*Primary Examiner* — J M Saint Surin
(74) *Attorney, Agent, or Firm* — Ostrager Chong Flaherty & Broitman P.C.

(57) ABSTRACT

A computer-controlled robotic platform with a collapsible lifting arm that positions a non-destructive inspection (NDI) sensor for scanning inside tunnel regions of a composite structure such as an integrally stiffened wing box. The lifting arm of a modified scissor lift mechanism can be collapsed to a very low height to pass through narrow sections of the integrally stiffened wing box, and also extended by more than a factor of three to reach the maximum height of the wing box tunnels. The system performs a vertical position sensing and control process that uses inverse kinematics to enable position control using data from a standard rotational encoder on the motor to determine vertical position. The system produces simulated encoder pulses that represent unit vertical displacements of a distal portion of a modified scissor lift mechanism using a forward kinematics equation in which the rotation angle of a lead screw is an input variable.

20 Claims, 12 Drawing Sheets

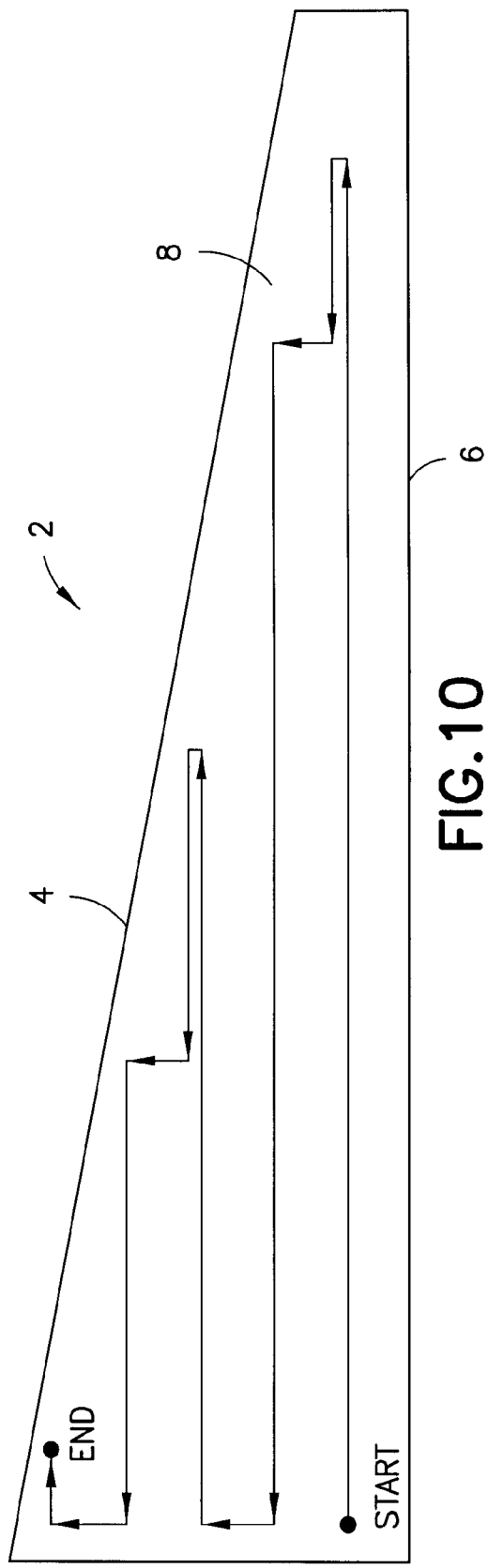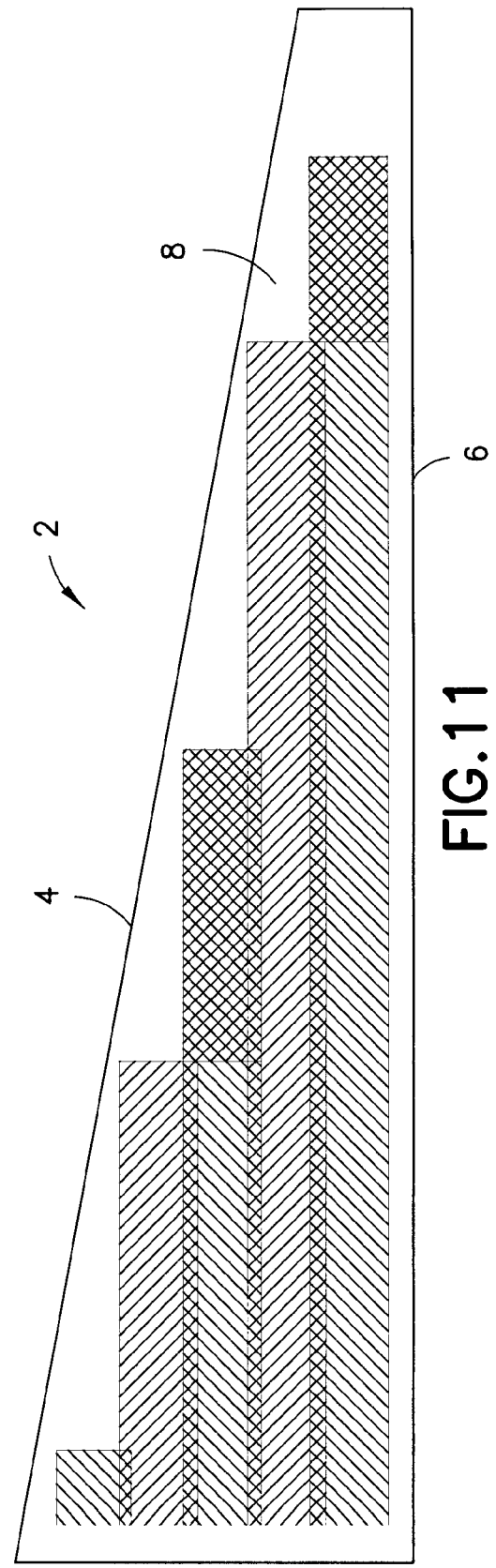

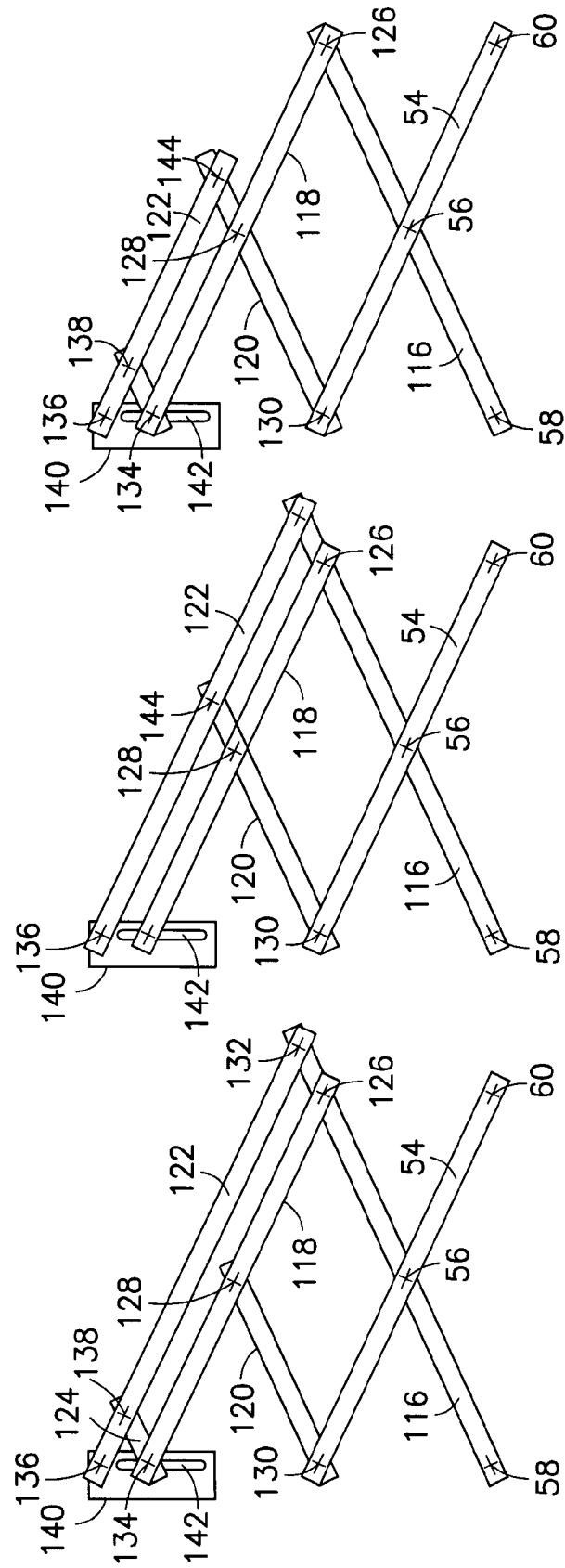

AUTOMATED INSPECTION OF SPAR WEB IN HOLLOW MONOLITHIC STRUCTURE

BACKGROUND

This disclosure generally relates to systems for carrying tools across surfaces, such tools including (but not limited to) sensors used in nondestructive inspection (NDI). In particular, this disclosure relates to systems for inspecting a long hollow structure having tapered internal cavities which are difficult to access, especially a structure made of composite material.

A variety of elongated composite structures may have relatively confined internal cavities that require inspection in order to assure that the structure meets production and/or performance specifications. One known elongated composite structure with tapering internal cavities is an integrally stiffened wing box for an airplane. The integrally stiffened wing box is primary structure and as such must be inspected to the required specifications to ensure structural integrity. Both the exterior and interior of each integrally stiffened wing box must be inspected in a production environment. For a production inspection, the inspection rate must be sufficient to meet the part production rate.

The exterior skins of a composite integrally stiffened wing box can be inspected by known conventional methods. Inspection of the vertical support elements (called "spars") at the part production rate is more challenging due to access limitations, tapering internal cavities, and varying part thickness. The filleted regions that form the transitions between the spar web (i.e., the flat central region of a spar) and the horizontal skins, as well as a small region directly adjacent to each fillet, are scanned by other systems. The problem of scanning the central area of each spar web requires a scanning system located within the confined spaces of long rectangular cavities or tunnels of the integrally stiffened wing box or similar structure. In the case of an integrally stiffened wing box, access is only available from the wider inboard end and the narrow outboard end.

Various prior approaches have been used to perform inspections of the wing box spars. A first approach was manual scanning, in which technicians moved the NDI scanning head over the surface manually. This had several limitations, including: low positioning accuracy and limited reach inside the wing box tunnels. A further prior approach is a single-transducer implementation based on a vehicle that supports a swing-arm device, with the swing arm pivot located on the vehicle at the proximal end of the arm and an ultrasonic transducer at the distal end of the arm. The vehicle moved along the part length from the inboard to the outboard end. During this travel, the swing arm moved the ultrasonic transducer in a vertical arc over the surface of the wall (spar), moving repeatedly back and forth between the upper and lower skins. Reversal of the swing arm motion at both ends of the vertical arc was accomplished using mechanical switches that acted against the upper and lower skins in succession, repeatedly. This device was slow not only because it employed a single transducer but also because the scan pattern involved a large number of motion reversals.

The foregoing solutions do not fully address the scope of the problem to be solved. Accordingly, there is a need for a remote computer-controlled apparatus that can access internal cavities or tunnels of an integrally stiffened wing box or similar elongated hollow structure and produce vertical and horizontal scanning motions of an ultrasonic NDI sensor array to facilitate the inspection of the central web portion of vertical support elements such as spars.

SUMMARY

The system disclosed herein is intended for use in the automated nondestructive inspection of the inside of large-scale hollow monolithic composite parts, the interior of which is not manually accessible, but has potential applications beyond conventional nondestructive testing. In particular, the system enables automated scanning of central areas of spar webs formed in an integrally stiffened wing box made of composite material.

In accordance with one embodiment, the system for scanning central portions of spar webs comprises an external motorized tractor, an internal active trailer vehicle that carries an NDI sensor, and an internal passive trailer vehicle. The trailer vehicles are magnetically coupled to each other through the spar web, while the trailer vehicles are magnetically coupled to the tractor vehicle through a surface skin of the integrally stiffened wing box. As the tractor vehicle is driven to travel along a desired path on the outer surface of the top or bottom skin, it pulls the inner trailer vehicles along. In accordance with an alternative embodiment, it may be possible to eliminate the tractor vehicle, instead providing the active trailer vehicle with its own horizontal drive motor and drive train for self-powered motion along the spar, assuming that gravity is sufficient to keep the trailer vehicles on the skin surface.

In accordance with one embodiment, the active trailer vehicle for scanning a central portion of a spar web is a computer-controlled robotic platform with a collapsible lifting arm that positions a tool, e.g., an array of NDI (e.g., ultrasonic) transducers (such array being referred to herein as a "sensor"), for scanning inside rectangular tunnel regions of an integrally stiffened wing box for an aircraft. More specifically, the mechanical design of the scanner includes a modified scissor linkage geometry that accommodates the limited clearance and widely varying geometry of the part interior. A computer-based control and position sensing system manages the nonlinear kinematics of that modified scissor lift mechanism. The active trailer for scanning the central portion of a spar web will be referred to herein as a "spar arm scanner".

Mechanical components of the spar web scanning system in accordance with one embodiment comprise a chassis-mounted modified scissor linkage type scan arm component which holds the ultrasonic array probe; and a passive trailer chassis component located on the opposite side of the spar web being inspected. These components are magnetically coupled through the spar web, thereby assuring that the scan arm chassis and ultrasonic array probe are held reliably against the web.

The disclosed system can be operated in a manual or an automated mode to follow a motion profile. Advantageous features of this system include at least the following: (1) the ability to collapse the payload-lifting arm to a very low height to pass through narrow sections of the integrally stiffened wing box, and also extend the arm by more than a factor of four to reach the maximum height of the transitioning wing box spars; and (2) the vertical position measurement and control process developed for the system uses kinematic equations of motion and data from a standard rotational encoder on the motor to determine vertical position and enable vertical position control. These features allow the system to work within the physical size limitations of hollow structures like an integrally stiffened wing box, while also allowing the system to be operated in wet environments associated with ultrasonic-based NDI scanning.

In accordance with one implementation, the central part of each spar web, which is decreasing in height from the inboard end to the outboard end, is inspected using a computer-controlled lifting arm that is mounted on a chassis of the spar arm scanner and can position a sensor at various commanded heights. This enables the system perform a type of raster scan of the central area of the spar web can be performed under computer control. This system can scan in both directions, so no time is wasted doing an unnecessary sweep back step.

Raster scanning of the central area of the spar web by the apparatus disclosed herein can be coupled with a strip scanner (not disclosed in detail herein) that mechanically follows a filleted join region and scans a strip-shaped area (e.g., 2 inches wide) along each spar edge. Because the strip scanner covers areas adjacent the filleted join regions at the top and bottom of the spar, the lifting arm of the spar arm scanner need not position the sensor close to those fillets. This significantly lessens the motion control complexity as compared to what would be necessary in the absence of this "buffer" strip. In addition, the lifting arm positions the sensor toward the wide inboard (or root) end of the spar. This means that scanning the root edge of a spar is not an issue. The tip end of the spar does not need its edge to be scanned because overlapping strip scans using a separate platform can be used to cover this area. An additional feature of the lifting arm is a camera mounted to give the operator a view of the scan head as it is operating. The lifting arm is designed so that the arm has sufficient reach to get to the top of the spar. The arm operates from the bottom.

One aspect of the subject matter disclosed herein is a method for moving a distal portion of a modified scissor lift mechanism to a target vertical position, the vertical position of the distal portion relative to a starting vertical position being a nonlinear function of rotation of a horizontal lead screw coupled to a motor, comprising: (a) calculating a lead screw rotation angle required to achieve a specified extension height of the modified scissor lift mechanism using an inverse kinematics equation in which extension height is an input variable; (b) instructing the lead screw motor to rotate the required number of turns to reach that the calculated lead screw rotation angle; (c) monitoring whether the number of lead screw motor rotations indicates that the target vertical position has been reached; and (d) stopping the motor when the target vertical position, as determined by lead screw rotation angle, has been reached. The method may further comprise computing and producing simulated encoder pulses that represent unit (equal size) vertical displacements of the distal portion of the modified scissor lift mechanism using a forward kinematics equation in which the angle of rotation of the lead screw is an input variable.

Another aspect is a mobile platform comprising: a frame; a first support block fixedly mounted to the frame; a second support block that is supported by and slidable relative to the frame a horizontal lead screw rotatably coupled to the first support block and threadably coupled to the second support block so that the second support block will move linearly (i.e. translate) relative to the first support block when the lead screw rotates; a motor coupled to the lead screw for driving rotation of the lead screw; a first link having a proximal end pivotably coupled to the first support block and a second link that is twice the length of the first link and having a proximal end pivotably coupled to the second support block, the first and second links being pivotably coupled to each other at the distal end of the first link and the midpoint of the second link, a vertical position of a distal end of the second link being a nonlinear function of rotation of the lead screw; and a payload platform pivotably coupled to the distal end of the second link, wherein the payload platform is translated in a direction perpendicular to the lead screw during rotation of the lead screw. A payload, for example, a tool, may be attached to the payload platform.

In accordance with a further aspect of the mobile platform described in the previous paragraph, the payload platform is also pivotably coupled to the distal end a third link that is the same length as the second link and runs parallel to the second link. The proximal end of the third link is pivotably coupled to the second support block, creating a parallelogram sub-linkage between the second support block, second link, payload platform, and third link.

A further aspect of the disclosed subject matter is a lifting system comprising: a horizontal lead screw; a motor coupled to the lead screw for driving rotation of the lead screw; a modified scissor lift mechanism coupled to the lead screw, a vertical position of a distal portion of the modified scissor lift mechanism being a nonlinear function of rotation of the lead screw; an encoder for measuring each rotation of the lead screw through a predetermined angle into a respective rotation encoder pulse, and a computer system programmed to control the motor in accordance with a motion control algorithm comprising: (a) calculating a lead screw rotation angle required to achieve a specified extension height of the modified scissor lift mechanism using an inverse kinematics equation in which extension height is an input variable; (b) instructing the lead screw motor to rotate the required number of turns to reach that the calculated lead screw rotation angle; (c) monitoring whether the number of lead screw motor rotations indicates that the target vertical position has been reached; and (d) stopping the motor when the target vertical position, as determined by lead screw rotation angle, has been reached.

Yet another aspect is a system comprising: a hollow composite structure comprising a spar web and first and second skins; a tractor vehicle disposed under the second skin, the tractor vehicle comprising a first frame, a plurality of wheels rotatably mounted to the first frame and in contact with the second skin, first and second magnet poles mounted on the first frame; a first trailer vehicle disposed above the second skin and on one side of the spar web, the first trailer vehicle comprising a second frame, a plurality of wheels rotatably mounted to the second frame and in contact with the second skin, a third magnet pole carried by the second frame and magnetically coupled to the first magnet pole through the second skin, a horizontal lead screw, a motor coupled to the lead screw for driving rotation of the lead screw, a modified scissor lift mechanism coupled to the lead screw, a payload platform pivotably coupled to a distal portion of the modified scissor lift mechanism, and a non-destructive inspection sensor mounted to the payload platform, wherein a vertical position of the distal portion of the modified scissor lift mechanism is a nonlinear function of rotation of the lead screw; and a second trailer vehicle disposed above the second skin and on another side of the spar web, the second trailer vehicle comprising a third frame, a plurality of wheels rotatably mounted to the third frame and in contact with the second skin, a fourth magnet pole magnetically coupled to the second magnet pole through the second skin. The first trailer further comprises a fifth magnet pole and the second trailer vehicle further comprises a sixth magnet pole magnetically coupled to the fifth magnet pole through the spar web.

Other aspects of apparatus and methods for automated scanning of the central portions of vertical webs inside elongated hollow structures are disclosed and claimed below.

BRIEF DESCRIPTION OF THE DRAWINGS

FIG. 10 is a diagram showing horizontal and vertical segments of motion path in accordance with one implementation.

FIG. 11 is a diagram showing central spar web area scan coverage in accordance with one implementation.

FIGS. 16A, 16B and 16C are diagrams showing multi-stage modified scissor mechanisms in accordance with alternative embodiments.

Reference will hereinafter be made to the drawings in which similar elements in different drawings bear the same reference numerals.

DETAILED DESCRIPTION

Figure 1:
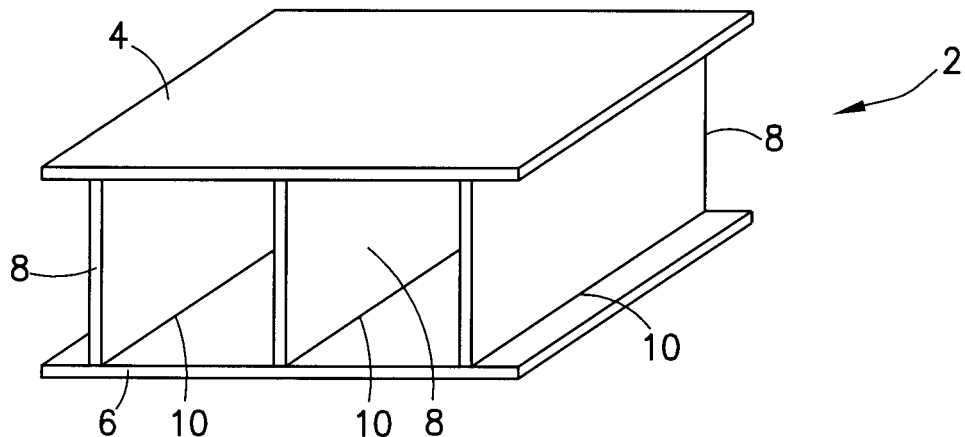
FIG. 1 is a diagram showing an orthographic view of a portion of a generalized integrally stiffened wing box of an airplane having top and bottom skins or panels connected by a plurality of spars.

In accordance with one embodiment, ultrasonic NDI sensors are used to inspect a hollow monolithic composite structure, such as an integrally stiffened wing box for an aircraft (e.g., a horizontal stabilizer). A portion of a generalized integrally stiffened wing box 2 for an aircraft is depicted in FIG. 1. The depicted integrally stiffened wing box comprises a top skin 4 and a bottom skin 6 connected by a plurality of a plurality of internal vertical support elements, hereinafter referred to as "spars". Each spar comprises a web 8 and respective pairs of filleted join regions 10 (also called "spar radii"), which connect the spar web 8 to the top and bottom skins. As used herein, the terms "top skin" and "bottom skin" refer to the relative positions of two skins of a wing box when the wing box is being inspected, not when the wing box is installed on an airplane (i.e., a wing box may be inverted for inspection).

The integrally stiffened wing box is primary structure of an airplane and as such much be inspected to ensure structural integrity. Inspecting large monolithic composite structures presents the following distinct, yet interrelated challenges. (1) The interior of the part is often inaccessible to conventional ultrasonic scanning systems. (2) The entire interior surface of the structure needs to be inspected. (3) The production manufacturing of composite structure for an active airplane program must be done at a rate that meets schedule commitments.

In accordance with one embodiment, special equipment and techniques can be used to transport the ultrasonic linear transducer array (also referred to herein as a "sensor") through the interior of the composite structure. For this type of inspection, the sensor is carried by a trailer vehicle (not shown in FIG. 1) placed inside the hollow volume of structure 2. This trailer vehicle can be characterized as being "active" in the sense that equipment it carries is actively performing a scanning function. The sensor needs to be acoustically coupled to each surface being inspected while an automated tractor vehicle (also not shown in FIG. 1) moves the trailer vehicle along that surface in a region of interest. This is accomplished by providing a column of water that flows between the sensor and the inspected part.

In FIG. 1, portions of the interior surfaces of the part which need to be inspected can be seen. Each spar needs to have all four filleted join regions 10 inspected and each web 8 inspected. This is a challenging inspection as each cavity is essentially a very long rectangular tunnel that for some wing box embodiments may decrease in cross section as one moves from the inboard end of the integrally stiffened wing box to the outboard end. The top and bottom skins 4 and 6 can be inspected from the exterior using conventional NDI techniques which are not part of this disclosure.

In accordance with one embodiment for inspecting structures of the type shown in FIG. 1, an external motorized and computer-controlled tractor vehicle is magnetically coupled to an internal active trailer vehicle that holds and positions one or more ultrasonic transducer arrays on the interior of the part. Also, there is an internal passive trailer vehicle on the opposite side of the spar that is magnetically coupled through the spar to the active trailer and also magnetically coupled through the skin to the tractor. This three-part system gives a very stable system for positioning and moving the ultrasonic transducers. One embodiment of such a three-part system will now be described with reference to FIGS. 2 and 3.

Figure 2:
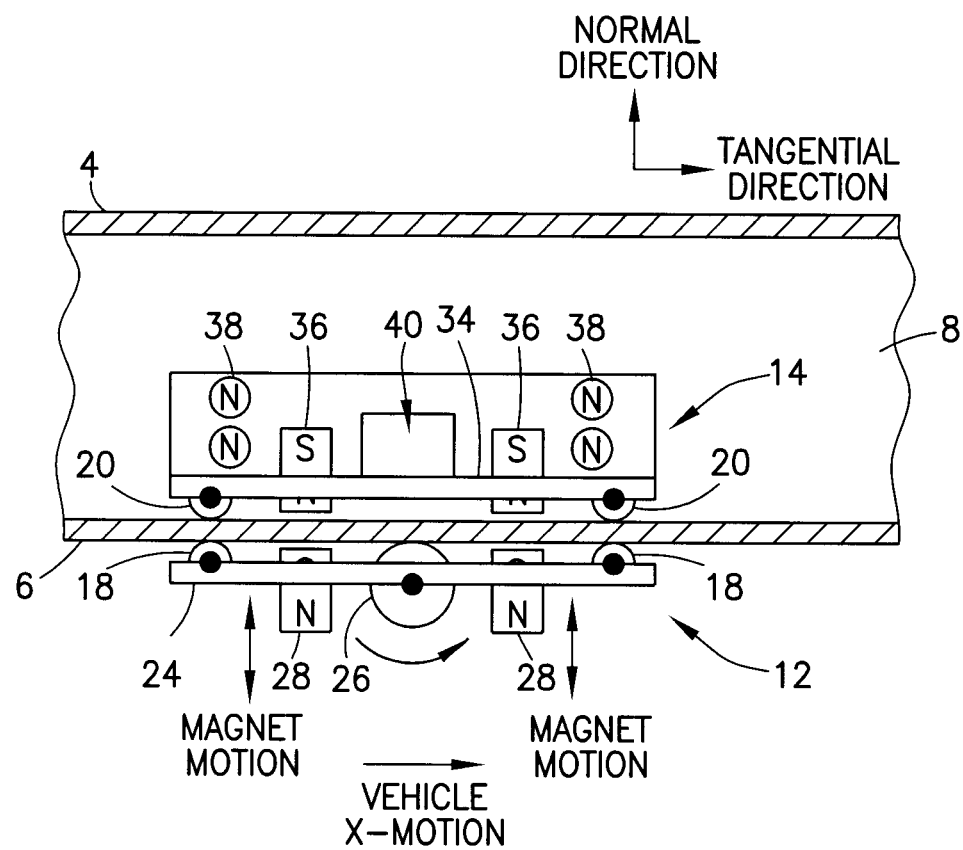
FIG. 2 is a diagram showing a side view of a tractor-trailer configuration that includes an active trailer vehicle above and a tractor vehicle below a bottom skin of an integrally stiffened wing box. (A passive trailer vehicle on the other side of the spar is not visible.)

FIG. 2 shows a side view of a tractor-trailer configuration in accordance with one embodiment (motor actuators and arm components are not shown). The automated inspection system comprises a traction-motor powered tractor vehicle 12, which rides on the external surface of bottom skin 6 of integrally stiffened wing box 2, and a pair of trailer vehicles (only trailer vehicle 14 is visible in FIG. 2, the other being hidden behind a spar web 8), which ride along an internal surface of the bottom skin 6.

Figure 3:
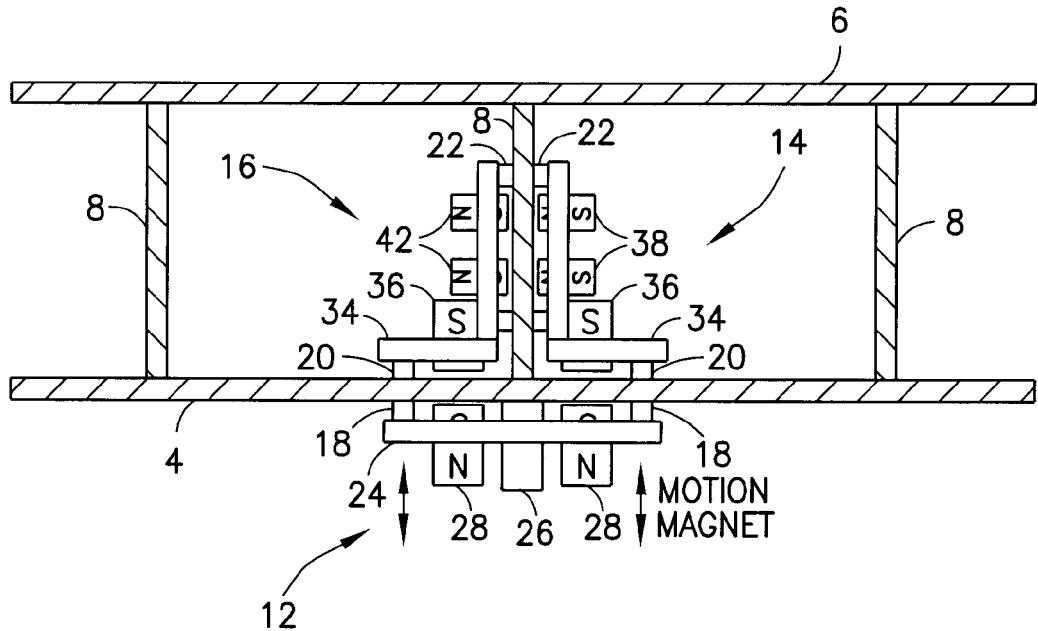
FIG. 3 is a diagram showing an end view of the tractor-trailer configuration depicted in FIG. 2.

FIG. 3 shows an end view of the tractor-trailer configuration depicted in FIG. 2, with inverted trailer vehicles 14 and 16 disposed on opposite sides of a spar web 8. As seen in FIG. 3, idler wheels 18 of tractor vehicle 12 contact and roll on the external surface of bottom skin 6 while idler wheels 20 of inverted trailer vehicles 14 and 16 (only one such idler wheel is visible in FIG. 3 for each trailer vehicle) contact and roll on the internal surface of top skin 4.

In accordance with the embodiment partly depicted in FIGS. 2 and 3, the tractor vehicle 12 comprises a frame 24. Four idler wheels 18 (only two of which are visible in each of FIGS. 2 and 3) are rotatably mounted to frame 24 in a conventional manner. The idler wheels 18 may be made of plastic and have smooth contact surfaces. Tractor vehicle motion is enabled by driving a drive wheel 26 (also rotatably mounted to frame 24) to rotate. Drive wheel 26 is coupled to a motor 30 via a transmission (not shown). The drive wheel 26 is positioned on the frame 24 so that it is in frictional contact with bottom skin 6 when idler wheels 18 are in contact with the same skin. The drive wheel is made of synthetic rubber material. The surface of the drive wheel may have a tread pattern. In addition, the tractor vehicle 12 carries multiple permanent magnets 28. Each permanent magnet 28 has North and South poles, respectively indicated by letters "N" and "S" in the drawings.

Still referring to FIGS. 2 and 3, the chassis of each trailer vehicle 14, 16 is comprised of a respective frame 34. For each trailer vehicle chassis, at least two vertical idler wheels 20 (only one of which is visible in FIG. 3) and at least four horizontal idler wheels 22 (only two of which are visible in FIG. 3) are rotatably mounted to frame 34 in a conventional manner. Each trailer vehicle 14, 16 further comprises multiple vertically mounted permanent magnets 36, the North poles of which are magnetically coupled to the South poles of confronting permanent magnets 28 carried by the tractor vehicle 12. In the design described by FIGS. 2 and 3, each trailer vehicle has two vertically mounted permanent magnets 36, but other designs may use different configurations.

As seen in FIG. 3, in addition to being magnetically coupled to the tractor vehicle 12, the trailer vehicles 14 and 16 are magnetically coupled to each other using additional sets of permanent magnets 38 and 42. As seen in FIG. 2, the trailer vehicle 14 comprises four horizontally mounted permanent magnets 38. The trailer vehicle 16 also comprises four horizontally mounted permanent magnets 42 (only two of which are visible in FIG. 3), the poles of which are respectively magnetically coupled to opposing poles of the permanent magnets 38 on trailer vehicle 14. This magnetic coupling produces an attraction force that holds idler wheels 22 of trailer vehicles 14 and 16 in contact with opposing surfaces of an intervening spar (shown in FIG. 3).

As seen in FIG. 2, the trailer vehicle 14 further comprises a payload 40. For the NDI scenario depicted in FIGS. 2 and 3, payload 40 is an ultrasonic NDI sensor which is acoustically coupled to the internal surface being inspected. For example, the inspected region is covered with a constant stream of water to acoustically couple the ultrasonic sensor to a spar web 8 or a filleted join region 10. Magnetically coupled systems are well suited for operation with water in the environment. The orientation and scanning movement of payload 40 will depend on which portion of the wing box internal surface is to be inspected.

As the tractor vehicle is driven to travel along a desired path on the outer surface of the top or bottom skin, it pulls the inner trailer vehicles along. The magnetic coupling system described above keeps the inverted tractor vehicle in contact with the surface it rides on. For wing box applications, two magnetically coupled trailer vehicles can be used, one on each side of the spar, as shown in FIG. 3. This allows the system to take advantage of the internal structure of the scanned object as a guide to allow the system to track properly along the surface.

The system partly depicted in FIGS. 2 and 3 further comprises means (not shown in FIGS. 2 and 3) for automatically adapting to the variable thickness of the intervening skin or panel (i.e., top skin 4 or bottom skin 6) by raising or lowering the magnets (which magnet motion is indicated by double-headed arrows in FIG. 2) on the tractor vehicle as it moves along the structure being inspected. Further details concerning the trailer-tractor configuration depicted in FIGS. 2 and 3 (and alternative embodiments) are disclosed in U.S. patent application Ser. No. 13/313,267, the disclosure of which is incorporated by reference herein in its entirety.

The basic concept of the tractor/trailer transport system described above can be adapted as necessary to perform different scanning operations, such as scanning the edge and central portions of each web 8 and the four filleted join regions 10 that join each web to the top and bottom skins (two at the top skin 4 and two at the bottom skin 6). While it is advantageous to use the same tractor for each of the different scanning operations that make up the overall inspection process, a different active trailer can be used to perform each respective specific scanning operation. This in turn may require the use of a respective passive trailer specifically adapted to magnetically couple with a respective active trailer. This disclosure will describe methods and apparatus for inspecting the central portions of the spar webs in an elongated and tapered hollow structure. The active trailer for scanning the central web portion of a spar will be referred to herein as a "spar arm scanner".

The spar arm scanner operates under computer control within vertical height restrictions and in wet environments. Also, the scanning system is intended for use in combination with other scanning processes that address scanning in the areas near the filleted regions of the spar. The spar arm scanner in accordance with one embodiment will be discussed in terms of mechanical design, kinematics, position sensing, and motion control.

Mechanical Design

Figure 4:
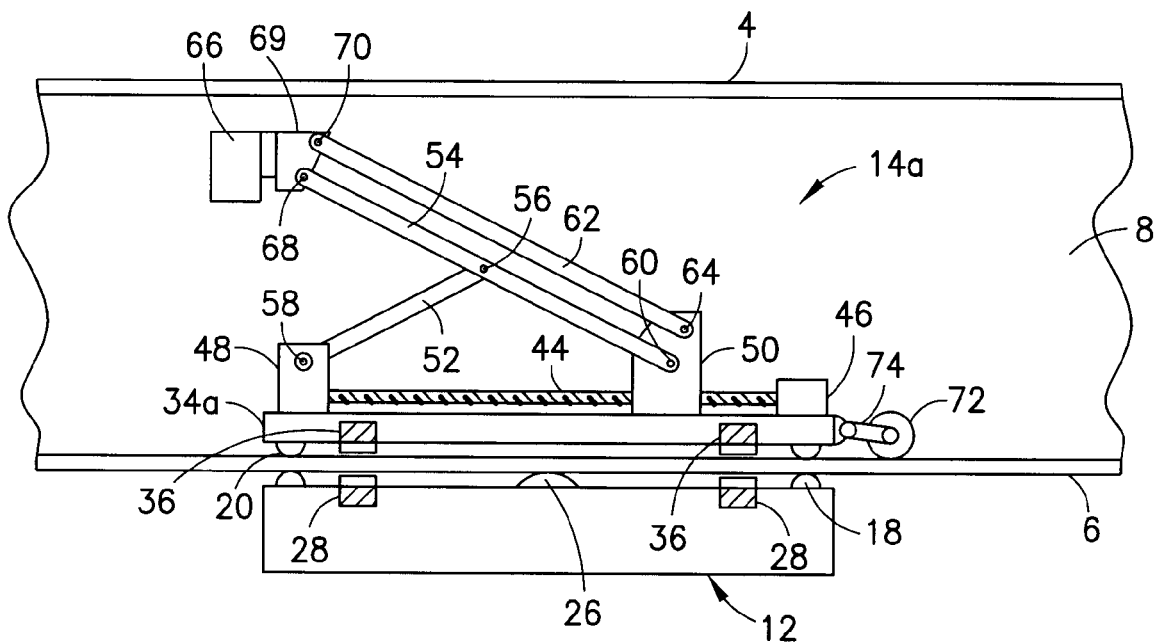
FIG. 4 is a diagram showing a side view of a tractor-trailer configuration that includes a spar arm scanner above and a tractor vehicle below a bottom skin of an integrally stiffened wing box. (A passive trailer vehicle on the other side of the spar is not visible.)
Figure 5:
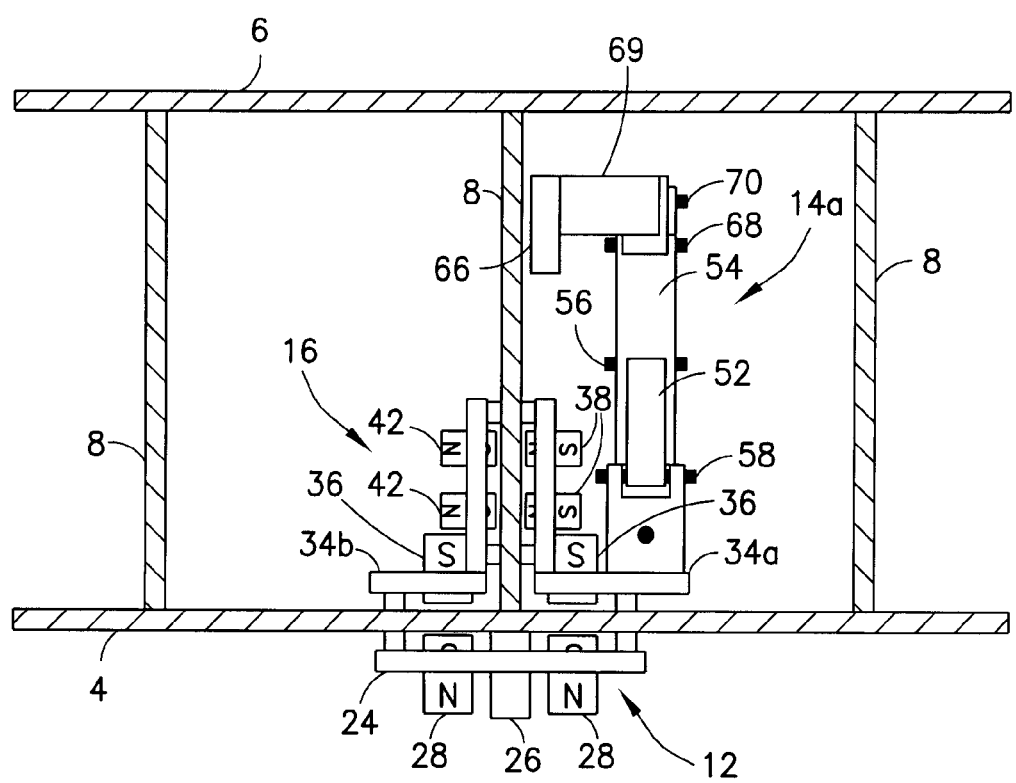
FIG. 5 is a diagram showing an end view of the tractor-trailer configuration depicted in FIG. 4.

FIG. 4 is a side view showing one embodiment of a spar arm scanner 14a magnetically coupled to a tractor vehicle 12. A passive trailer vehicle 16 (not visible in FIG. 4) can be seen in the end view of FIG. 5.

Referring to FIG. 4, the spar arm scanner 14a is magnetically coupled to and pulled by tractor 12. The arm scanner 14a comprises magnets 36 which are coupled to opposing tractor magnets 28 through a bottom skin 6. Trailer-to-trailer coupling magnets are also part of the system, but are not shown in FIG. 4. The spar arm scanner 14a carries a payload 66 for non-destructive inspection of a web 8. The X-position of arm scanner 14a (and the payload it carries) is measured by an X-direction encoder (not shown in FIG. 4), which measures the rotation angle of an encoder wheel 72 mounted on the end of an encoder swing arm 74. The encoder swing arm 74 is pivotably coupled to trailer frame 34a of arm scanner 14a. The encoder wheel 72 rides on the inner surface of the bottom skin 6 as arm scanner 14a travels along a filleted join region.

The spar arm scanner in accordance with the embodiment shown in FIG. 4 further comprises a single-stage modified scissor lift mechanism (also known as a scissor linkage mechanism) with one degree of freedom, which is driven by a lead screw 44 and a programmable stepper motor 46. The modified scissor lift mechanism comprises a support block 48 mounted to a vehicle frame 34a and a translatable (relative to frame 34a) support block 50 (hereinafter "slider mechanism"). The lead screw 44 has a distal end rotatably coupled to support block 48 and an intermediate portion rotatably coupled to slider mechanism 50 by a nut (not shown), which is attached to the latter. The stepper motor 46 is mounted to frame 34a. An output shaft of stepper motor 46 is coupled to the other end of lead screw 44. The slider mechanism 50 is put into motion by means of the lead screw 44 and stepper motor 46.

The modified scissor lift mechanism further comprises one link 52 having a length half that of another link 54. Link 52 is attached to a pivot point (first revolute joint) 56 midway along the length of the longer link 54, which will be referred to hereinafter as the "drive link". [A revolute joint (also called pin joint or hinge joint) is a one-degree-of-freedom kinematic pair used in mechanisms. Revolute joints provide single-axis rotation.] The other end of the shorter link 52 is pivotably coupled to support block 48 by a second revolute joint 58, and one end (referred to herein as the proximal end) of the drive link 54 is pivotably coupled to slider mechanism 50 through a third revolute joint 60. The slider mechanism 50 moves joint 60 towards or away from joint 58. The motion path of block 50 is a straight line defined by the axis of lead screw 44. In this configuration, the motion of the proximal end of drive link 54 causes orthogonal motion of its other end (referred to as the distal end) relative to the motion of the slider block 50. For the measurement task that this system is has been designed for, the proximal end of the drive link being driven by the lead screw moves horizontally, while the distal end moves vertically.

Although the position paths that both the proximal and distal ends of the drive link segment take are both linear (i.e., perfectly horizontal and perfectly vertical, respectively), the relative relationship between input and output velocities is not linear. This non-linear relationship between the input and output velocities has an impact on the motion control of this system, which will be described in detail later.

In addition to the long and short links of the single-stage scissor lift mechanism, a follower link 62, of equal length to drive link 54, is used to form a four-bar parallelogram linkage with the drive link 54 as one of the links. (This aspect of the system produces a "modified scissor lift mechanism", as described herein.) This additional link allows the system to maintain a constant orientation of the payload platform 69 located at the distal end of the drive link. Follower link 62 is pivotably coupled to slider mechanism 50 by a revolute joint 64. The payload platform 69 is pivotably coupled to the distal ends of links 54 and 62 by respective pin joints 68 and 70. During operation, as the proximal end of drive link 54 is driven by lead screw 44 from one end point of travel to the other, the payload platform motion will always stay perpendicular to the lead screw 44 and the orientation will stay constant. In other words, as slider mechanism 50 is moved toward support block 48, payload 66 (which is attached to the payload platform 69) moves up along a vertical path without rotating. In the current implementation of this design, the lead screw 44 is installed in parallel with the vehicle frame 34a, resulting in motion of the payload platform 66 being perpendicular to the frame 34a, which itself rides on wheels 20 that position the frame 34a parallel to the surface of the object being scanned.

This configuration will meet the dimensional constraints and motion requirements for the scanning application.

In another embodiment, for system configurations where gravity keeps the trailers firmly in contact with the bottom skin, if the X-direction motions of spar arm scanner were self-powered (and the tractor vehicle were eliminated), then the trailer vehicles would not need through-skin magnets and means for adjusting their positions.

Kinematics Analysis

Figure 6A:
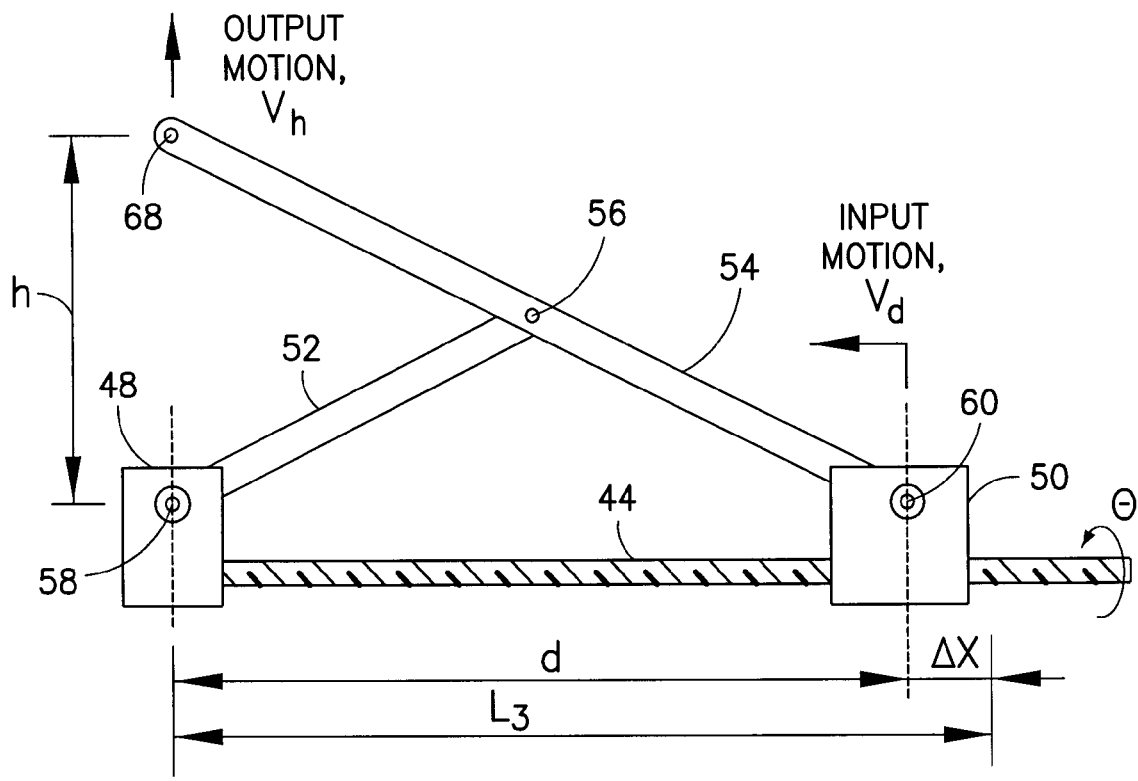
FIGS. 6A and 6B are diagrams respectively showing partially extended and retracted positions of a drive link in accordance with the four-bar parallelogram linkage shown in FIG. 4.
Figure 6B:
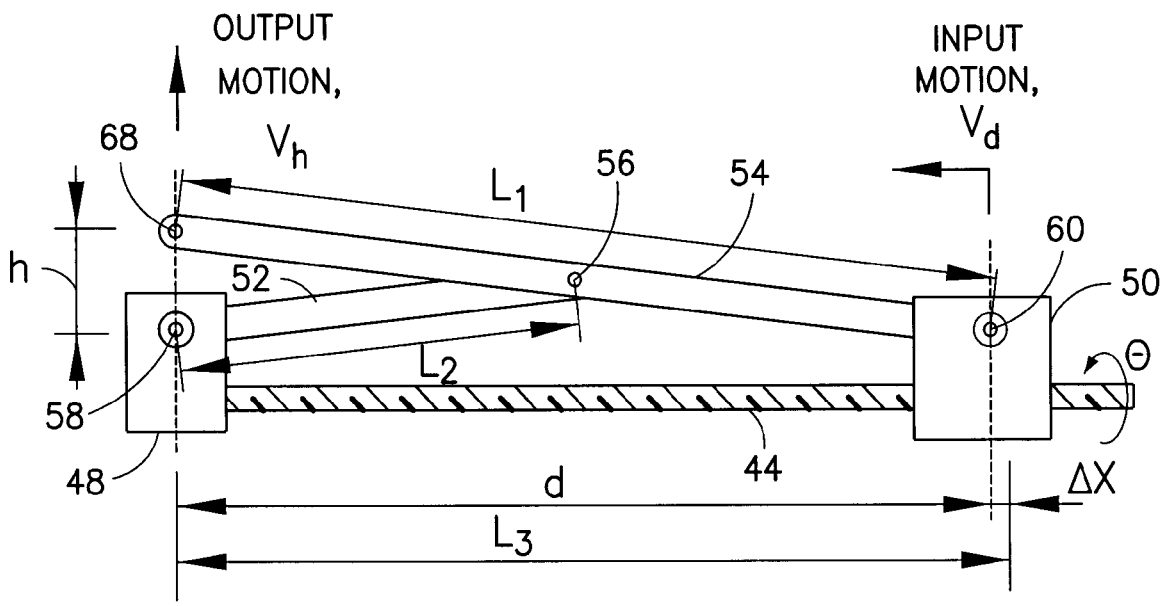

In order to design the type of control system needed to accurately position the payload platform, an analysis of the linkage kinematic motion needs to be performed. FIGS. 6A and 6B show the scissor linkage components of the assembly depicted in FIG. 4. (For this system, since the motion of link 62 matches that of link 54; it is not shown in FIG. 6A or FIG. 6B, and is not needed in the following derivation.) FIG. 6A shows the drive link 54 in a partially extended position; FIG. 6B shows it in an almost fully retracted position. FIG. 6B also indicates various dimensions, where $L_1$ is the length of drive link 54 (i.e., the distance between the axes of revolute joints 60 and 68); $L_2$ is the length of link 52 (i.e., the distance between the axes of revolute joints 56 and 58) and is half the length of $L_1$ ($L_2=L_1/2$); $L_3$ is distance between revolute joints 58 and 60 in the fully retracted kinematic position and is equal to $L_2$; d is the current distance between the axes of revolute joints 58 and 60; h is the distance between the axes of revolute joints 58 and 68; and $\Delta X$ is the change of distance $L_3$ from its maximum length ($d=L_3-\Delta X$). In FIGS. 6A and 6B, $V_h$ and $V_d$ represent the vertical output velocity and horizontal input velocity respectively.

Figure 7:
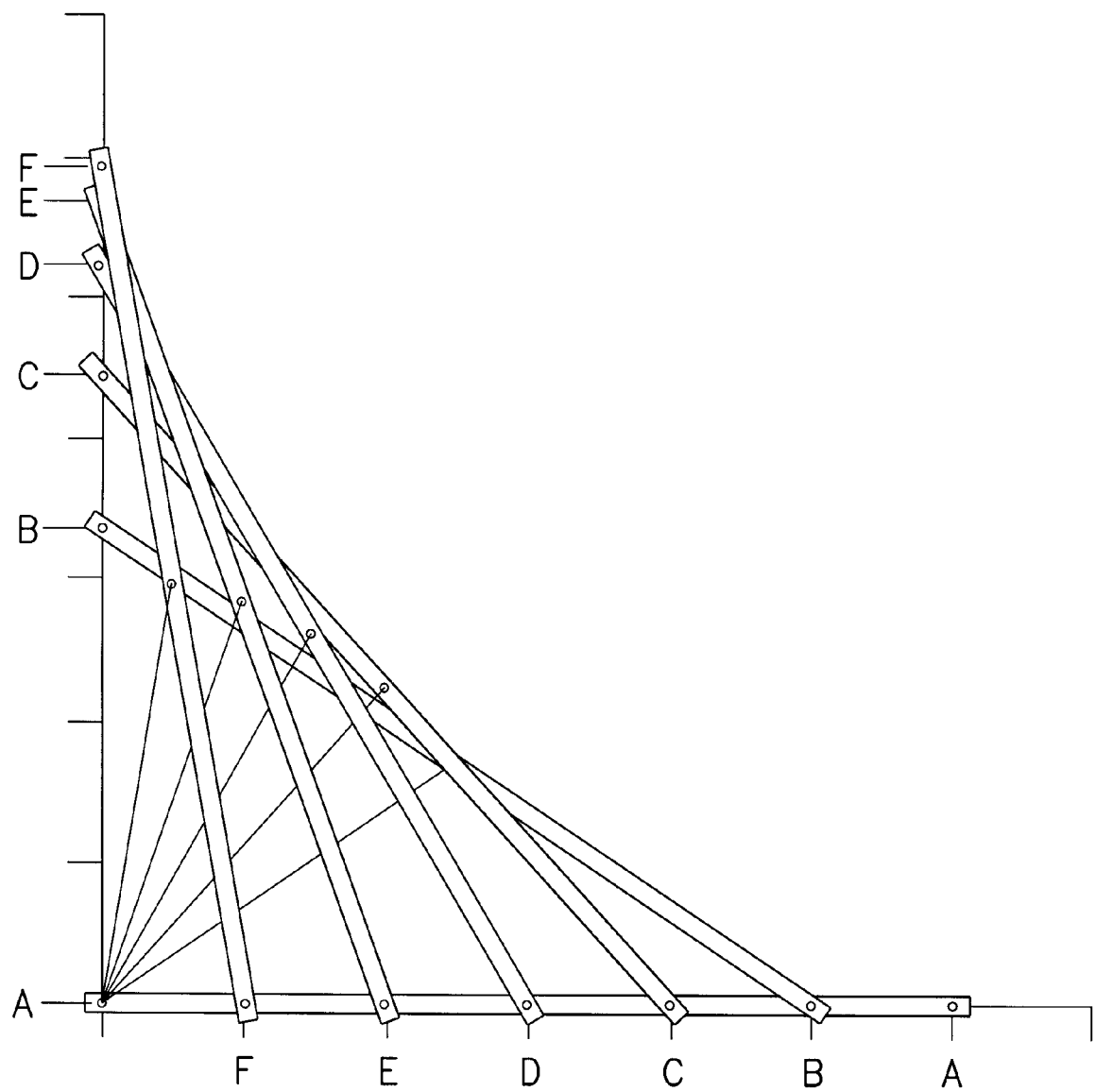
FIG. 7 is a diagram showing intermediate positions of the drive link shown in FIG. 4.
Figure 8:
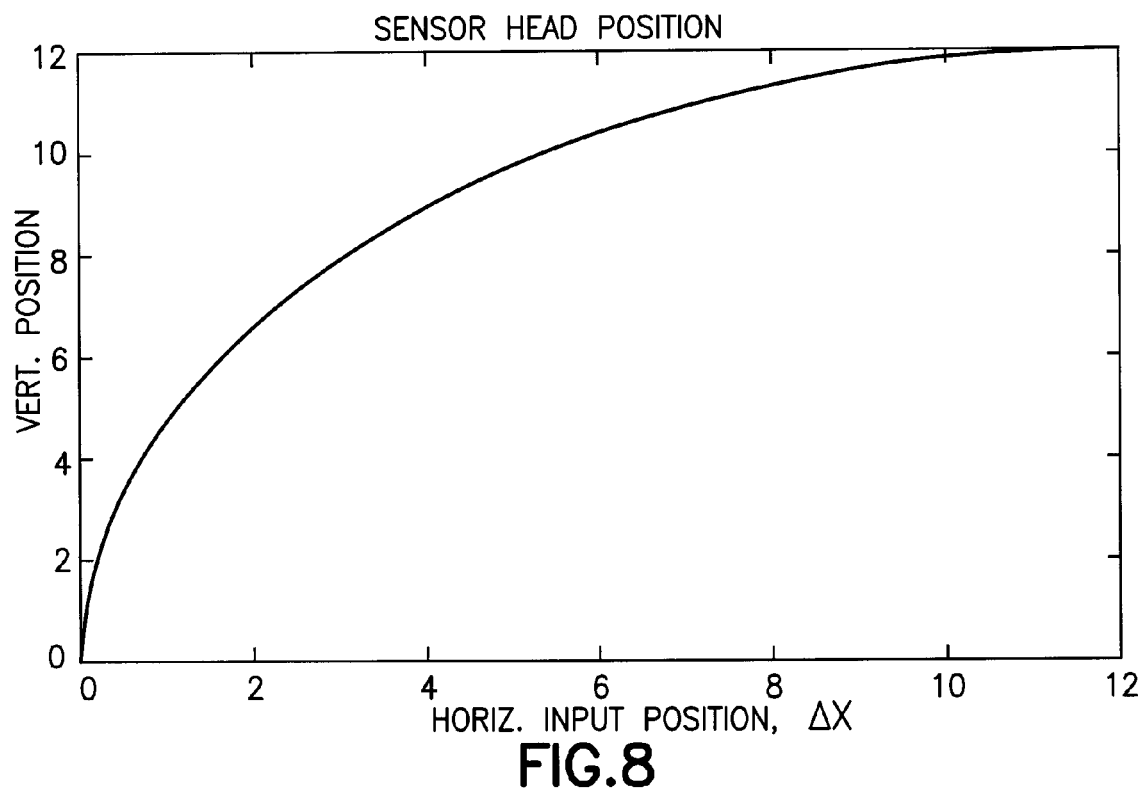
FIGS. 8 and 9 are graphs that respectively plot sensor head position and velocity versus horizontal input position for a single-stage modified scissors lift mechanism.
Figure 9:
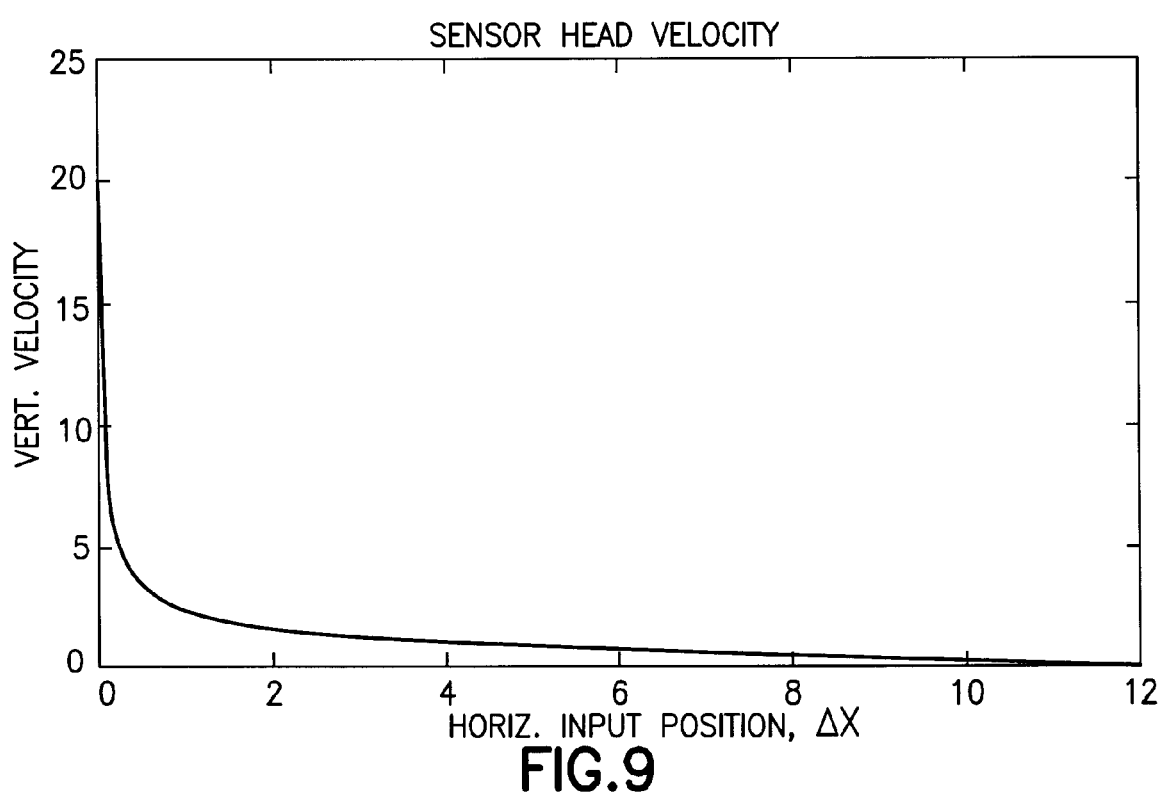

FIG. 7 shows multiple intermediate positions of the drive link as it is moved though its range of motion. The labeled positions (A, B, C, etc.) on the input end of the link, shown on the horizontal axis, correspond to the same labels for positions on the output (vertical) axis. Notice that the spacing on the input axis is uniform, but is non-uniform on the output axis. This non-linear relationship is also shown in the position and velocity plots in FIGS. 8 and 9 respectively. More specifically, FIG. 8 is a plot of the vertical output position h versus the horizontal input position d; while FIG. 9 is a plot of the vertical output velocity $V_h$ versus the horizontal input position d for a constant input velocity.

Since the output motion (position and velocity) of the lifting arm is not proportional to the input motion (i.e., non-linear), the control of the output position of the payload platform is not as simple as just counting the rotations of the lead screw and applying a scale factor. In order to move the payload to precise position a more complex control method is needed.

In order to control this mechanism, knowledge of the equations of motion of the mechanism can be used to develop a non-linear transfer function that describes the vertical position of the payload in terms of rotations of the lead screw throughout the entire range of motion. For this option, the stepper motor 46 and a lead screw rotary encoder (not shown in FIG. 4) are far away from the water (and enclosed in housing for additional protection). This leaves the task of developing a process to convert lead screw rotations into vertical positions. To mathematically describe the relationship between the input and output motions, a non-linear transfer function needs to be developed. Not only must the vertical motion of the payload platform be described in terms of the lead screw rotations; the inverse function which describes lead screw rotations in terms of the vertical position of the payload platform is also needed. In robotics applications, defining the output Cartesian position in terms of an input actuator variable (position or rotation) is usually called forward kinematics, and defining the input actuator variable position or rotation in terms of the output Cartesian position is called inverse kinematics. The derivation of these functions will be described next.

From knowledge of the scissor lift mechanism, it can be seen that the input drive motion and output vertical position form the sides of a right triangle. The relationship between the sides of a right triangle is described by the Pythagorean Theorem: $a^2+b^2=c^2$. In the situation under discussion, a is the distance d between the two lower pivot points 58, 60, where b is the height of the payload platform (more specifically, the distance between the axis of revolute joint 58 and the axis of revolute joint 68 as seen in FIG. 6A); and c is the length $L_1$ of the drive link. Using this relationship the forward kinematics equations (with the variable names from FIG. 6B) is:

$$h = \sqrt{L_1^2 - d^2} \quad (1)$$

where the distance change from maximum length is: $d = L_3 - \Delta X$, and the displacement $\Delta X$ is: $\Delta X = k\theta$, where k is the lead screw thread pitch. The linkage length constraint is: $L_3 = L_1$. Substituting these variables into Equation (1) results in:

$$h = \sqrt{2L_1 k\theta - (k\theta)^2} \quad (2)$$

which is the forward kinematics transfer function that describes the height, h, in terms of the constants $L_1$ (drive link length) and k (lead screw pitch), and the rotation variable $\theta$ (lead screw angle).

The inverse kinematics equation is:

$$\theta = (L_1 - \sqrt{L_1^2 - h^2})/k \quad (3)$$

which describes the required lead screw angle $\theta$ in terms of the constants $L_1$ (drive link length) and k (lead screw pitch).

Note that in applications were multiple scissor stages are used, the height is calculated by multiplying the right side of Equations (1) and (2) listed above by the number of scissor stages in the mechanism, and dividing the h term in Equation (3) by the number of stages. With the foregoing type of control system, the positioning requirement can be met.

Motion Path Planning

Motion paths are loaded into the control software at runtime as a file that contains the individual horizontal and vertical motion segments (along with other calibration, velocity, and timing instructions). FIG. 10 shows an example motion path with multiple horizontal and vertical path segments. In this example, the motion path starts at the left end of the wing box tunnel produces a stair-step pattern that fits into the internal shape of the integrally stiffened wing box. Smaller vertical steps may be programmed to get better coverage. Alternatively, the horizontal and vertical segments could be changed concurrently.

FIG. 11 shows the resulting coverage area, where the cross-hatching lines "lean" in the direction of motion. Notice that there is some overlap in the coverage area. This is acceptable and even desirable in some areas to protect the overall motion plan against gaps in coverage. Overlap is handled properly by the scanning software application.

Control and Position Sensing Implementation

Figure 12:
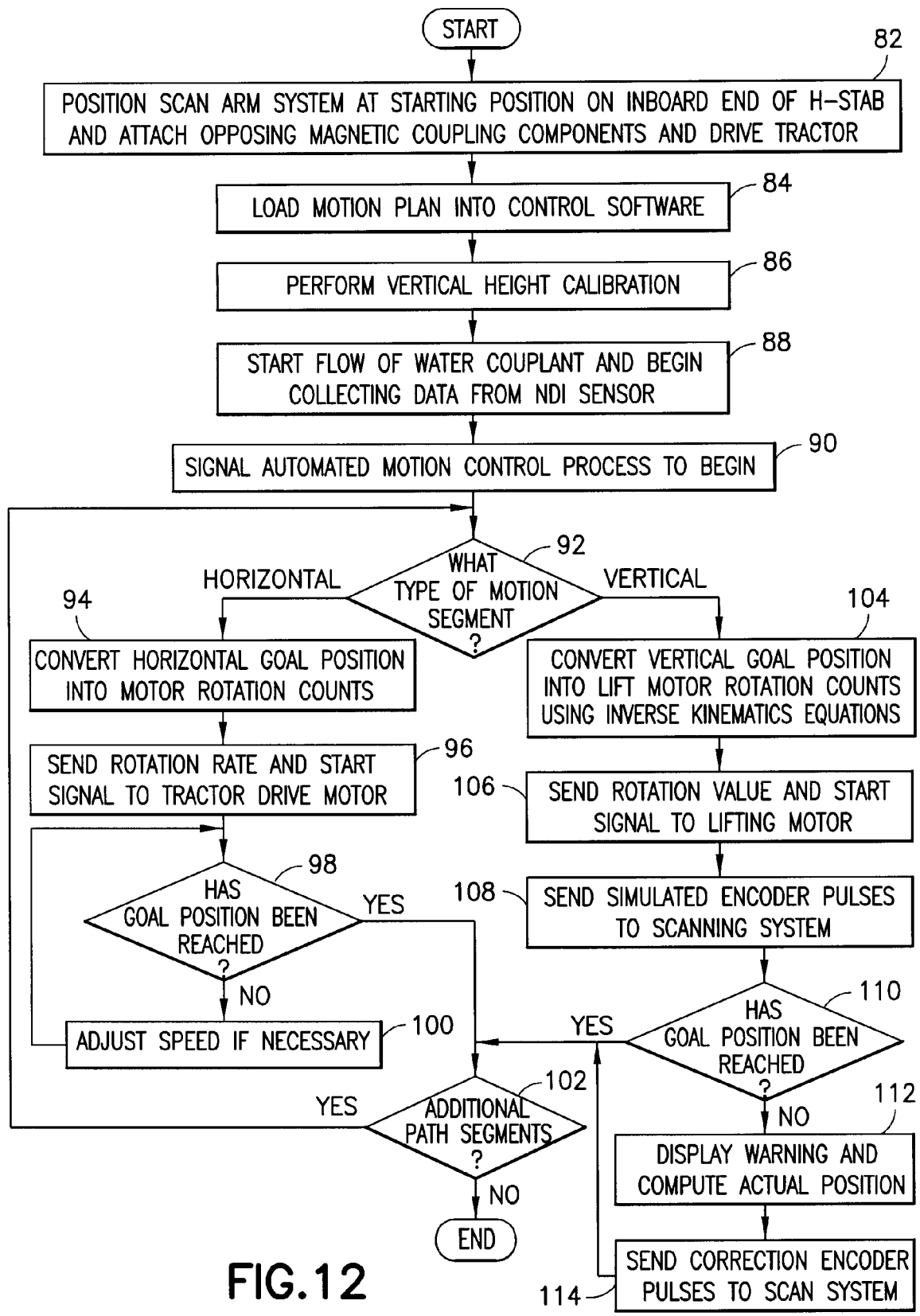
FIG. 12 is a flowchart showing operations performed during setup and scanning in accordance with one implementation.

The above-described system positions the payload (NDI sensor) at specific locations while moving the payload at specified velocities. It also provides the horizontal and vertical positions of the payload to NDI scan software application running on a control computer. To achieve the foregoing, motion control and position measurement processes must be implemented in software using available motor control interfaces and knowledge about the kinematics of the lifting arm. A flowchart showing the system operation during wing box inspection is given in FIG. 12.

In step 82, the scan arm system is placed at a starting position on the inboard end of the integrally stiffened wing box and the tractor and trailer vehicles are magnetically coupled as previously shown in FIG. 3. Before or after step 82, a motion plan is loaded into the control software application (step 84). After the vehicles are in position, a vertical height calibration is performed (step 86). After the flow of water has been turned on, the collection of data from the NDI sensor is started (step 88). The operator then signals the automated motion control process to begin (step 90). The motion control process then determines what type of motion path segment, horizontal or vertical, is called for by the loaded motion plan (step 92).

If the next motion segment should be horizontal, the horizontal goal position is converted into a motor rotation count (step 94). The rotation rate and a start signal are then sent to the tractor drive motor (step 96). During motion in the X-direction, the motion control process determines whether the horizontal goal position has been reached (step 98). If not, then the speed is adjusted if necessary (step 100). If the horizontal goal position has been reached, the process determines whether additional motion path segments need to be executed (step 102). If not, then the motion control process terminates. If additional motion path segments need to be executed, the process returns to step 92. If the motion control process determines that the next motion segment should be horizontal, the sequence of steps described in this paragraph is repeated.

If the motion control process determines that the next motion segment should be vertical, the target vertical position is converted into a lift motor rotation count using inverse kinematic equations (step 104). Then the rotation value and a start signal are sent to the lifting motor (step 106); and simulated encoder pulses are generated and sent to the scanning system (108). During vertical motion, the motion control process determines whether the target vertical position has been reached (step 110). If not, a warning is displayed on user interface and the actual vertical position of a specified point on the modified scissor linkage mechanism (e.g., a revolute joint axis) is computed (step 112). Corrected simulated encoder pulses are then sent to the scanning system (step 114). The motion control process then performs step 102. Alternatively, step 102 is performed if step 110 determines that the target vertical position has been reached.

The motion control process will repeatedly return to step 92 until step 102 determines there are no additional motion path segment. This enables the automated system to follow the loaded motion plan, such as the plan indicated in FIG. 10. The horizontal motion of the tractor vehicle and the vertical motion of the payload relative to the trailer vehicle can be controlled to provide the area scan coverage shown in FIG. 11 or other coverage schemes.

Horizontal and Vertical Motion Control.

Commercially available stepper motors have existing position and velocity control modes, but neither of these modes is perfectly suited for the type of control needed for horizontal position control in the above-described application. In the motor manufacturer's existing interface, the velocity mode by itself does not allow precise positioning, and the control of velocity in the position mode is limited and does not allow the level of adjustment during motion sequences that is needed. So a hybrid solution for horizontal control was developed using the motor velocity mode and information from an external encoder.

The horizontal motion control objective for this system is to move the magnetically coupled vehicles at a constant velocity (rate) and come to a stop at a specified goal position. In a horizontal motion control process in accordance with one implementation, the motor manufacturer's velocity control mode is supplied in the low-level motion control firmware by setting the desired velocity, while a separate proportional-integral-derivative (PID) closed-loop feedback process using data from the external encoder is included by the high-level motion control software to modify the velocity at run-time to make sure that the trailer vehicle comes to a stop at the desired location. The process is implemented using an encoder that measures the rotation of a surface contact wheel (item 72 in FIG. 4) that is rotatably coupled to the frame of the spar arm scanner 14*a*.

The vertical control uses a different approach. In this part of the application, precise control of the velocity profile of the vertical motion is not required, so the standard position control available from the motor control interface can be used, with the addition of a final position check to make sure that the number of rotations requested was completed. For vertical motion the number of rotations needed is not a direct linear function of the height, so the inverse kinematics equations of motion described earlier are used to compute the required number of motor turns needed to achieve the desired height.

Position Sensing.

Horizontal and vertical position data describing the location of the sensor head relative to a starting point on the integrally stiffened wing box are needed by the scan application in order to correctly align the data coming from the elements of the NDI sensor. This data is provided to the scan application in terms of encoder pulses (with quadrature or direction information). In the present system arrangement, a wheel rotation encoder measures the horizontal position of the trailer vehicle and is sent directly to the scan application, but the vertical measurement (as described above) is more complex due to the non-linear kinematics of the arm motion and requires a different type of implementation.

Since the system does not directly measure the height with an encoder, a separate method of generating the position pulses is required to feed vertical position data to the NDI scanner hardware. From the point of view of the NDI scanner hardware, it does not know how the pulses are generated, only that they arrive in the format that matches the output from an encoder. This means that if the motion measurement and control system can be setup to create pulse sequences with frequency and amplitude that are within the same range of operation as a standard digital encoder, then the NDI scanning system will have no idea that the data is not coming from an encoder, and no alterations in the way the scan hardware and software works will be needed. From a digital signal communications standpoint, there is no difference between this type of "virtual encoder" and a physical encoder.

As described in detail earlier, the kinematic equations of motion for the arm provide the non-linear relationship between the horizontal displacement created by the rotation of the lead screw motor and the desired height of the payload; from this relationship the number of turns of the lead screw can be computed to achieve the required height of the payload. At the same time, the simulated encoder pulses corresponding to the vertical displacement can be generated by the data acquisition device and transmitted to the NDI scanning software.

One option for controlling the number of rotations of the lead screw motor for vertical motion uses internal motor steps plus and internal encoder check; another option is to use an external encoder attached to the motor shaft (which is coupled to the lead screw).

For the first option, a control computer instructs the stepper motor that drives the lead screw to rotate a specific number of steps and then sends the stepper motor a command to send back the internal encoder position. This option does not use the internal motor encoder data in a continuous manner; instead the computer requests a single position when motion has stopped using a motor API command (through a serial interface). This approach is useful if a particular stepper motor is used that does not output the raw internal encoder data directly. (Note that if a different stepper motor were used that could provide direct output from an internal encoder, then the process similar to the one described in the next paragraph could be utilized). As the motor movement command is executing, a data acquisition device connected to the control computer sends out simulated quadrature encoder pulses to the NDI scanning system. These pulses are based on the vertical displacement from the initial position, as computed from the kinematics equations and the number of turns of the lead screw motor. In this type of control using a stepper motor movement and a final position check, the rate of simulated encoder pulses is controlled independently of the motor. This means that while the arm is moving, the pulses are an approximation of the actual arm height, but will be correct at the end of the motion. If the arm does not reach the final destination due to a disturbance, the final position check will be used to synchronize the current height with the pulses sent.

For the second lead screw motor control option, an encoder is coupled to the stepper motor shaft in such a way that the encoder generates a pulse for each unit rotation (i.e., a specified number of degrees or fraction of a degree) of the shaft. The control computer does not read the encoder data itself (since it may not be using a real-time operating system and could miss counts); instead the encoder data is read by a real-time data acquisition device, which is then sent over a serial-type of interface (RS232/422) to the computer. The data acquisition device is connected to the control computer running a software application that takes the input signals and uses the mechanism kinematics equations to generate output quadrature pulses that are identical in form to what an encoder would produce. These simulated quadrature pulses are output by the data acquisition device and sent to the scanning system, e.g., to an ultrasonic pulser/receiver (which then sends the simulated pulses to an NDI scan application which is running on the control computer). The scanning system treats those simulated quadrature encoder pulses as if they were pulses from a physical vertical position encoder. With this type of arrangement, the current height of arm is continuously synchronized with the simulated encoder pulses.

Note that in situations where a data acquisition unit is not available to provide simulated encoder counts, a hybrid solution using a string encoder setup as shown in FIG. 17A or 17B (described in detail below) could be used to augment the open-loop inverse kinematics solution by providing encoder counts directly to the NDI scanner hardware.

Vertical Height Calibration

To ensure that the system produces accurate vertical positions, it first must be calibrated. Since the system uses a rotational encoder, an absolute number of rotations from zero is not available unless a starting rotation value is set based on a known position of some part of the system. From a kinematics point of view, the simplest zero point would be when the mechanism is fully collapsed. But this configuration is problematic, since it would not be possible to extend the mechanism when all of the links are parallel (which would require infinite force), and for some component layouts, it is not possible to have all of the links in parallel. For these reasons, the system has an initialization point somewhere other than the zero vertical position. This non-zero initial position can be seen in FIG. 6B, where the initial distance $d_{init}$ of revolute joint 60 from pin joint 58 corresponds to the non-zero vertical position of pin joint 68 relative to pin joint 58.

To calibrate the system with a kinematically non-zero location, a switch (e.g., a Hall Effect sensor) can be used to indicate when the lifting arm has reached a known vertical position. Knowing this position, the inverse kinematics equations for the lifting arm can be solved to produce the required horizontal position of the drive pivot (i.e., revolute joint 60 in FIG. 4) and rotational angle of the lead screw.

In the above-described system, the indicator switch is positioned at the lower range of the acceptable travel of the lifting arm to also function as a motor cut-off (limit) switch. Using the switch in this position produces some complicating factors. In this position the system has greater elastic deformation (especially when carrying a payload), and the backlash in the drive train causes the system to move to slightly different positions when it is being driven to a point from different directions. To address these problems, a process was developed to compute an offset correction value for the location of the limit switch.

The offset value is computed by driving the arm to a vertical position in the middle of the operating range of the arm using the nominal switch position value in the forward kinematics equations. At this point a measurement is made using a separate measurement instrument (such as a caliper) to determine the actual vertical position. This measurement is then used in the inverse kinematics equations to solve for the required horizontal position (and lead screw angle) needed to achieve this position. The difference between the horizontal position computed by the inverse kinematics using the measured vertical position, and the horizontal position computed using the desired vertical position input by the user, is the horizontal offset error. The new "equivalent" indicator switch position is computed by using forward kinematics with the sum of the horizontal offset error and the initial horizontal offset. This process only needs to be performed once when the initial position of the limit switch is set.

Control System

Figure 13:
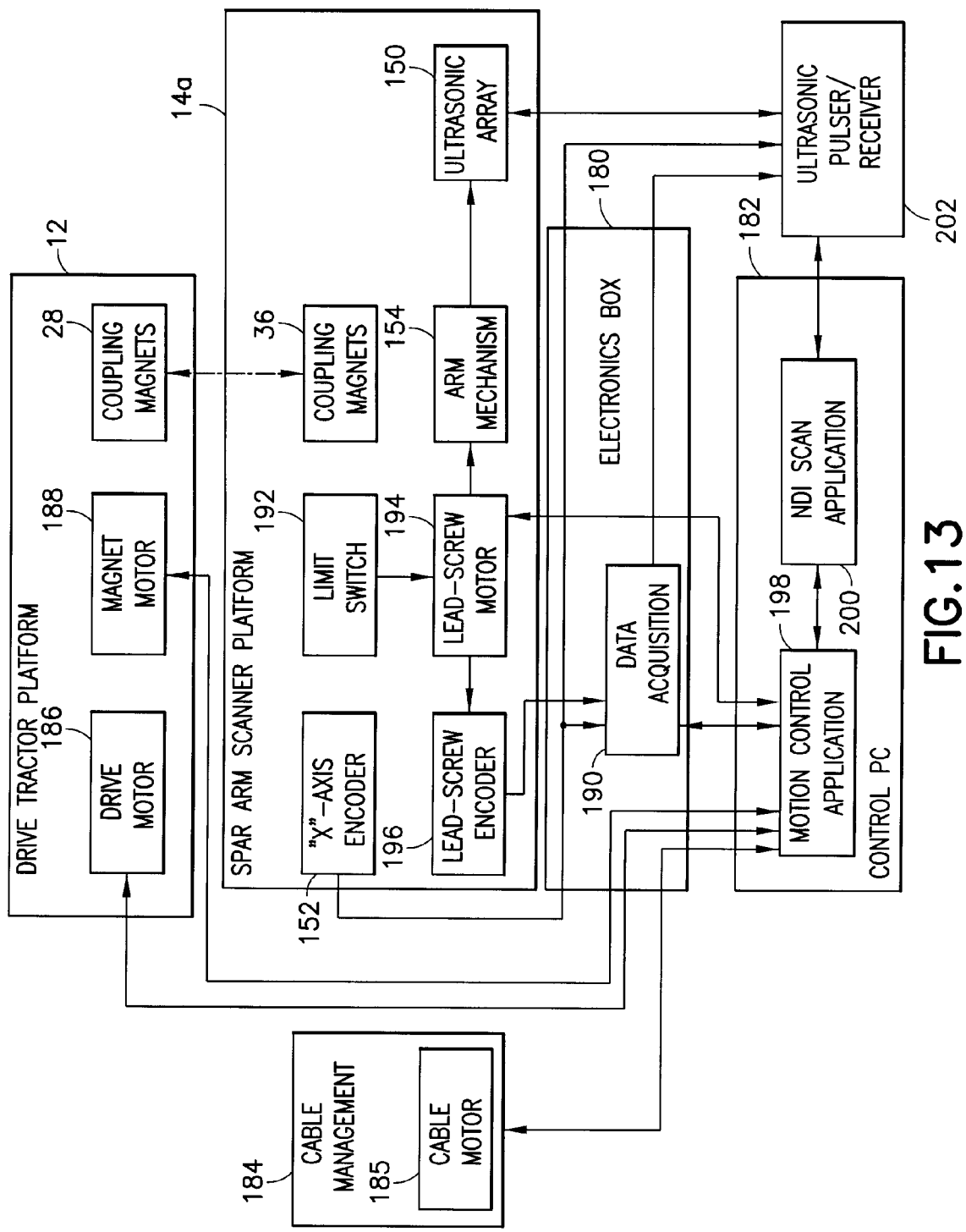
FIG. 13 is a block diagram showing a control system in accordance with one embodiment.

FIG. 13 is a block diagram showing some components of a control system in accordance with one embodiment. The control system comprises a ground-based computer 182 programmed with motion control application software 198 and NDI scan application software 200. The control computer 182 is connected to the drive tractor platform (previously referred to as a "tractor vehicle") 12 and to the spar arm scanner (previously referred to as an "active trailer vehicle") 14*a* by flexible electrical cables that connect to an electronics relay/switch box 180. The electronic relay/switch box 180 contains the system power supplies, relays, and a data acquisition device 190, and integrates all the scanner control connections and provides an interface between the computer and the tractor 12, spar arm scanner 14*a* and cable management system 184.

The computer 182 may comprise a general-purpose computer programmed with motion control application software 198 comprising respective software modules for controlling drive motor 186 and magnet vertical positioning motors 188 onboard the tractor platform 12. The magnet motors 88 displace the tractor coupling magnets 28 as disclosed in U.S. patent application Ser. No. 13/313,267.

Motion control application software 198 also controls a lead screw motor 194 that causes a modified scissor lift (i.e., arm) mechanism 154 to produce specified vertical motions of the ultrasonic transducer array 150. The range of vertical motion of the ultrasonic transducer array 150 in both directions is limited by limit switches 192. In accordance with one embodiment, a lead screw encoder 196 measures the angular position of the output shaft of lead screw motor 194, which angular position in turn determines the height of the ultrasonic transducer array 150 effectuated by the arm mechanism 154. The motion control application software 198 is capable of moving array 150 vertically and tractor 12 magnetically coupled to spar arm scanner 14*a* horizontally (i.e., in the X-direction) independently, either in sequence or concurrently. The position of the spar arm scanner in the X-direction is indicated by pulses output by an X-axis encoder 152.

In accordance with one embodiment, the encoded data from both encoders 152 and 196 is received by a data acquisition device 190 via a relay switch and a splitter (not shown) inside the electronics box 180. The data acquisition device 190 also has digital input and output connections that are used for multiple functions within the system. The data acquisition device 190 converts the lead screw encoder data into quadrature encoder pulses that simulate the pulses which would be outputted if a vertical position encoder were arranged to output pulses representing the vertical position of a distal end of the scanner arm. For the web arm scanning sub-system, the arm height value is computed by the motion control software kinematics equations and then the data acquisition device 190 is instructed by the motion control software 198 to generate the corresponding quadrature pulses (which are sent out of the data acquisition device 190 through digital output ports). These simulated encoder pulses are sent to the ultrasonic pulser/receiver 202. The ultrasonic pulser/receiver also receives pulses generated by the X-axis encoder 152 via the aforementioned switch and splitter (not shown in FIG. 13) inside the electronic box 180. The pulser/receiver 202 sends the encoder pulses to the NDI scan software 200. The NDI scanning software application interprets the simulated encoder pulses as a height value, which is used (along with the X-encoder values) to position the scan data in the proper location.

The computer 182 hosts ultrasonic data acquisition and display software that controls the ultrasonic pulser/receiver 202. The ultrasonic pulser/receiver 202 in turn sends pulses to and receives return signals from the ultrasonic transducer array 150. The NDI scan application software 200 controls all details of the scan data and the display of data. The pulser/receiver 202 correlates the acquired ultrasonic data with the X-encoder 152 and simulated encoder information received from the data acquisition device 190.

The motion control application software 198 also controls a motor 185 of a cable management system 184. There are several cables that need to accompany the scanner and the tractor down the length of the box being inspected. The cable management system automatically feeds out the cables or pulls in the slack as the vehicles move. The cable management system 184 consists of two sets of motorized wheels that grip the cables. The cable motor 185 is under computer control by way of control PC 182 and motion control software 198, which synchronizes the cables with the movement of the active trailer and the tractor, extending or retracting the cables as appropriate.

One Implementation

Figure 14:
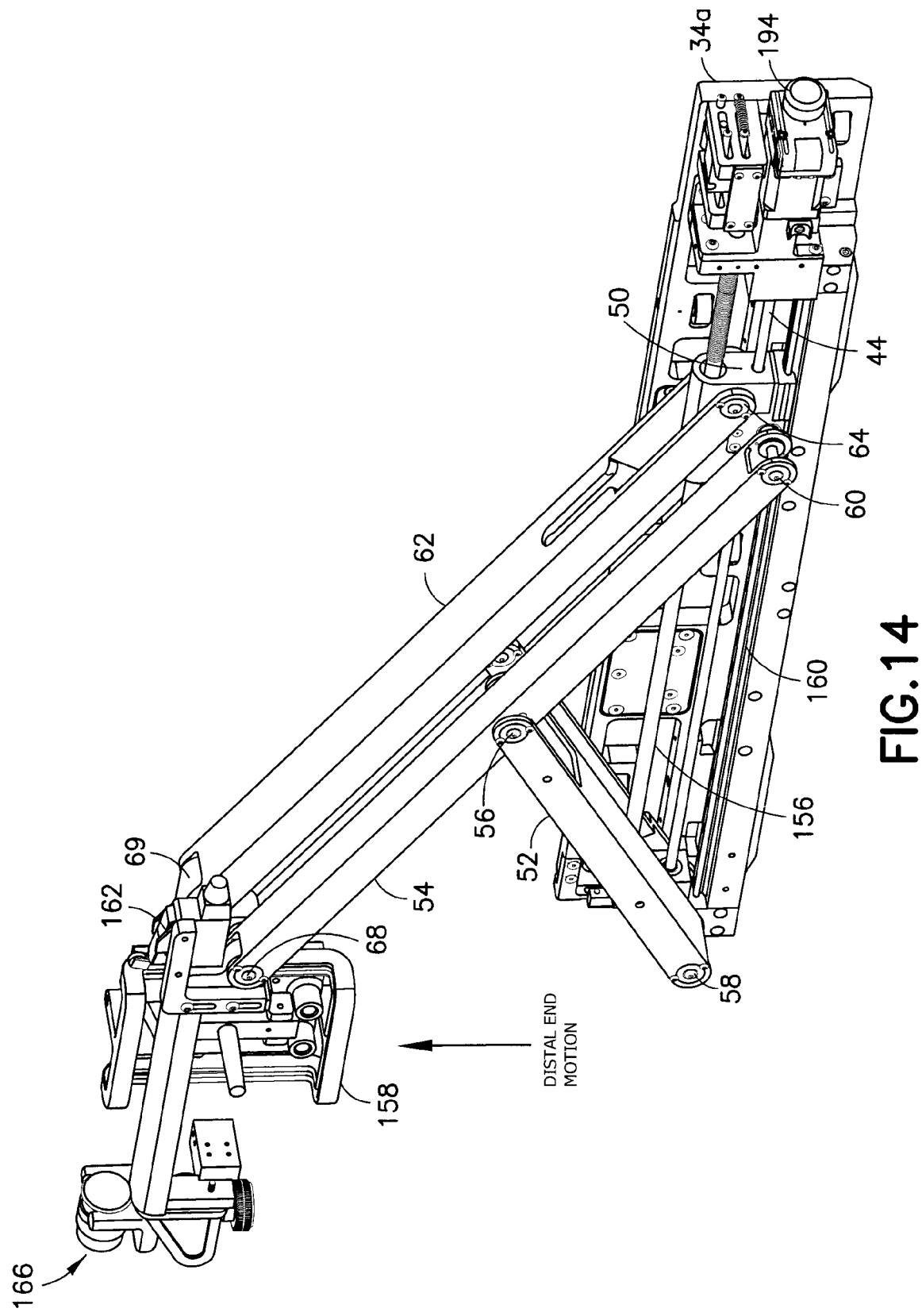
FIG. 14 is a diagram showing an isometric view of a spar arm scanner in accordance with one implementation.

Components of a spar web scanning system in accordance with one implementation will now be described with reference to FIG. 14. This implementation of a spar arm scanner comprises a scan arm assembly which is mounted on a chassis. The spar arm scanner chassis comprises a frame 34*a* that supports a rotating lead screw 44, which driven to rotate by a programmable stepper motor 194 mounted on one end of frame 34*a*. The spar arm chassis further comprises a fixed rod 156 and a fixed rail 160 which are mounted to frame 34*a* in parallel with the lead screw. A slider mechanism 50 is slidable on rail 160 and along rod 156 during rotation of lead screw 44.

The scan arm assembly comprises links 52, 54 and 56. (The movements of these links during lead screw rotation have been previously described with reference to FIG. 4.) The proximal ends of links 54 and 62 are rotatably coupled to slider mechanism 50 by respective revolute joints 60 and 64. In this implementation, the drive link 54 is laterally displaced relative to slider mechanism 50 and follower link 62, which allows revolute joint 60 to be placed at an elevation lower than the elevation of the lead screw 44. A NDI probe assembly 158 is rotatably mounted to payload platform 69, which is connected to the distal ends of links 54 and 62. A camera assembly 166 is attached to the NDI probe assembly. When the distal end of drive link 54 reaches its uppermost position, that event is detected by an upper limit switch 162; when the distal end of drive link 54 reaches its lowermost position, that event is detected by a lower limit switch 164 mounted on frame 34a.

Other Implementation Items

Since it is not possible to observe the lifting arm when it is inside the wing box tunnels, a lightweight video camera can be attached to the arm to monitor its operation. The power and video signal are sent through an umbilical cable bundle that also carries power and command connections to the system, as well as the signals from the encoder and NDI sensor back to the operator workstation.

With respect to alternate positioning solutions, using closed-form inverse kinematics to solve for the current vertical position of the payload platform based on the number of turns of the lead screw (measured by a standard rotational encoder on the motor) provides a reliable solution, with few moving parts. Alternatively, a system could be developed in which a position sensor, such as a string encoder, is used to directly measure the vertical position. This position data could then be used in a closed-loop feedback control system. One of the problems with this approach is that in the environment where this system will be used, the NDI sensor requires a water-couplant interface. This means that the vertical position sensor will get wet. Most string encoders have accuracy and reliability problems in wet environments. In this application it would be difficult to completely protect the position sensor from the water.

Figure 15A:
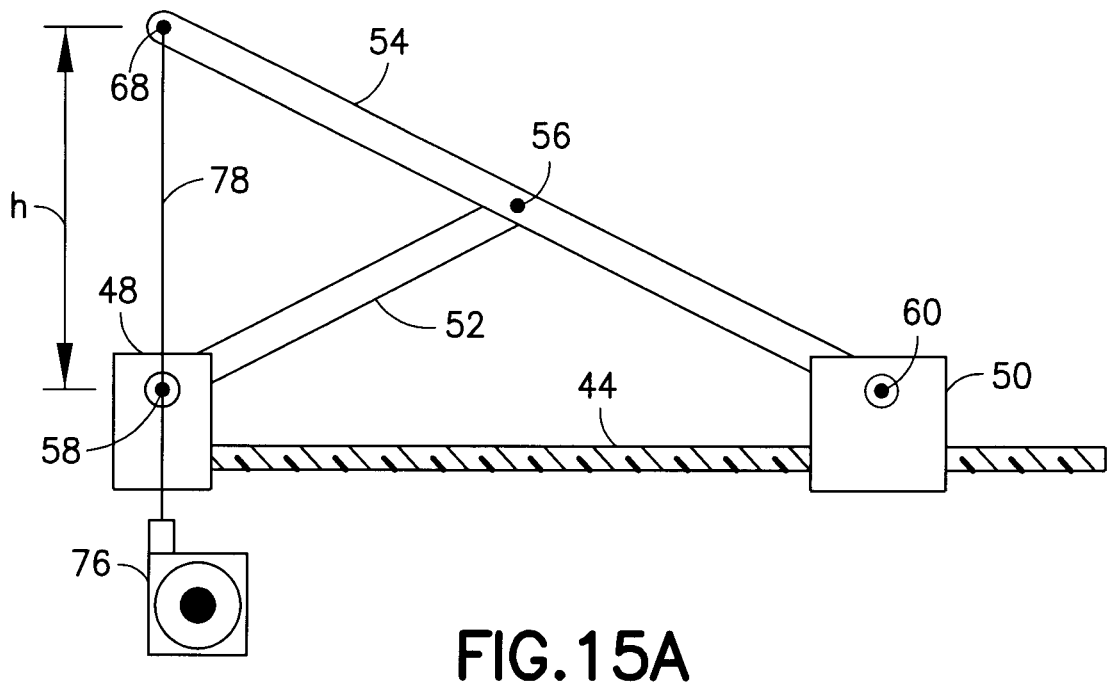
FIGS. 15A and 15B are diagrams showing respective spar arm scanner designs in accordance with alternative embodiments that use a string encoder to determine the vertical position of the payload.
Figure 15B:
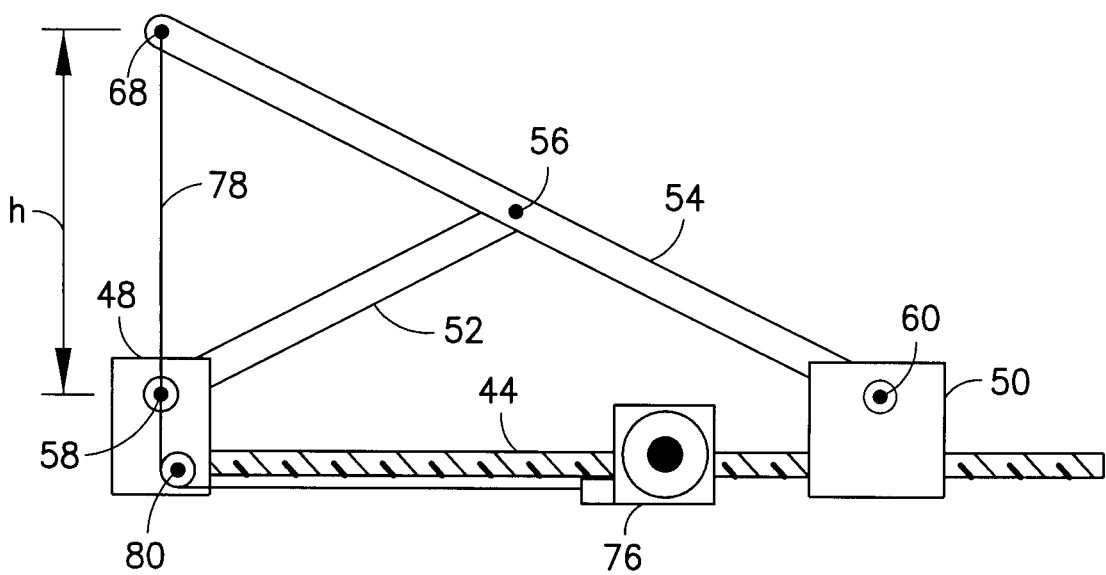

FIGS. 15A and 15B show alternate solutions that use a string encoder 76 that measures the displacement of a string 78 connected to the distal end of drive link 54 (i.e., pin joint 68). The string encoder 76 is fixedly attached to the trailer frame (not shown in FIGS. 15A and 15B). The string encoder 76 seen in FIG. 15B is in front of, not coupled to the lead screw 44. In the embodiment shown in FIG. 15A, the string 78 extends vertically between pin joint 68 and string encoder 76. In the embodiment shown in FIG. 15B, the string 78 wraps around a pulley 80 (pivotably mounted to pivot block 48) and runs horizontally from pulley 80 to string encoder 76. Either embodiment would meet the vertical measurement requirement, but using a string encoder presents other difficulties associated with placement and the wet environment. Even though the design in FIG. 15B would place the string encoder 76 away from the location where water is present, it requires more moving parts (with more weight) and requires a closed-loop feedback control loop for accurate positioning.

Alternative mechanical designs include multi-stage scissor linkage mechanisms having two or more stages. Using a multi-stage scissor linkage mechanism, the height ratio of the fully extended position to the retracted position can be increased as needed. FIGS. 16A-16C show respective alternative embodiments of double-scissor stack configurations with equivalent payload motion.

The mechanism shown in FIG. 16A comprises: a drive link 54 that is pivotably coupled to a translatable support block (not shown) by means of a revolute joint 60; and a second link 116 which is attached to a revolute joint 56 midway along the length of drive link 54. The proximal end of the second link 116 is pivotably coupled to a stationary support block (not shown) by means of a revolute joint 58. The modified scissors mechanism further comprises: a third link 118 (parallel to drive link 54) having a proximal end pivotably coupled to the second link 116 by means of a revolute joint 126; and a fourth link 120 (parallel to link 116) is attached to a revolute joint 128 midway along the length of the third link 118. A proximal end of the fourth link 120 is pivotably coupled to a distal end of drive link 54 by means of a revolute joint 130. A follower link 122 (parallel to link 118) has a proximal end pivotably coupled to the distal end of the second link 116 by means of a revolute joint 132. A short fifth link 124 (parallel to links 116 and 120) is pivotably coupled to links 118 and 122 by means of respective revolute joints 134 and 138. The distal end of link 122 is coupled to a payload platform 140 at a pin joint 136. The platform 140 has a vertical slot 142. The revolute joint 134 is attached to a pin (not shown) that is captured in slot 142. As the double-scissor mechanism shown in FIG. 18A extends and retracts, the pin attached to revolute joint 134 moves up and down in slot 142. This pin-slot joint prevents rotation of payload platform 140 as it moves up or down along a vertical path.

The embodiment shown in FIG. 16B differs from that shown in FIG. 18A in that link 124 in the latter has been eliminated, the distal end of link 118 has an attached pin (not shown) that rides in slot 142, and link 120 has been extended so that its distal end is pivotably coupled to follower link 122 by a revolute joint 144.

The embodiment shown in FIG. 18C differs from that shown in FIG. 18A in that links 116 and 122 in the latter have been shortened and link 120 has been extended so that its distal end is pivotably coupled to the proximal end of follower link 122 by a revolute joint 144.

In accordance with a further alternative embodiment, for system configurations where gravity keeps the trailers firmly in contact with the bottom skin, instead of being magnetically coupled to a motorized tractor vehicle below the bottom skin and a passive trailer on the other side of the spar, the spar arm scanner can be motorized, in which case the arm scanner could drive itself along the spar web while being magnetically coupled to the passive trailer on the other side thereof. In this embodiment, the tractor vehicle can be eliminated.

In addition to NDI-specific types of inspection, other types of inspection or manufacturing applications may be able to take advantage of the mechanical and control concepts presented here. For example, the NDI sensor carried by the payload platform can be replaced by other components, such as: laser scanners, video cameras, robotic manipulators, reflective targets, paint heads, or other electro-mechanical components.

While various embodiments have been described, it will be understood by those skilled in the art that various changes may be made and equivalents may be substituted for elements thereof without departing from the scope of the teachings herein. In addition, many modifications may be made to adapt a particular situation to those teachings without departing from the scope thereof. Therefore it is intended that scope of the claims set forth hereinafter not be limited to the disclosed embodiments.

As used in the claims, the term "computer system" should be construed broadly to encompass a system having at least one computer or processor, and which may have two or more interconnected computers or processors.

Furthermore, the method claims set forth hereinafter should not be construed to require that the steps recited therein be performed in the order in which they are recited.

The invention claimed is:

1. A mobile platform comprising:
a frame;
a first support block fixedly mounted to said frame;

a second support block that is supported by and slidable relative to said frame;

a horizontal lead screw rotatably coupled to said first support block and threadably coupled to said second support block so that said second support block will move linearly relative to said first support block when said lead screw rotates;

a motor coupled to said lead screw for driving rotation of said lead screw;

a first link having a proximal end pivotably coupled to said first support block and a second link that is twice the length of the first link and having a proximal end pivotably coupled to said second support block, said first and second links being pivotably coupled to each other at a midpoint of said second link, a vertical position of a distal end of said first link being a nonlinear function of rotation of said lead screw; and a payload platform pivotably coupled to said distal end of said first link, wherein said payload platform is translated in a direction perpendicular to said lead screw during rotation of said lead screw.

2. The mobile platform as recited in claim 1, further comprising a tool attached to said payload platform.

3. The mobile platform as recited in claim 1, further comprising a third link having a proximal end pivotably coupled to said second support block, wherein said second and third links are mutually parallel and said payload platform is pivotably coupled to distal ends of said second and third links.

4. The mobile platform as recited in claim 3, further comprising:

first and second joints which respectively pivotably couple said proximal ends of said second and third links to said second support; and third and fourth joints which respectively pivotably couple said distal ends of said second and third links to said payload platform, wherein the axes of said first through fourth joints are located at respective vertices of a parallelogram.

5. The mobile platform as recited in claim 2, wherein said tool comprises an ultrasonic transducer array.

6. A method for moving a distal portion of a modified scissor lift mechanism to a target vertical position, the vertical position of the distal portion relative to a starting vertical position being a nonlinear function of rotation of a horizontal lead screw coupled to a motor, comprising:

(a) calculating a lead screw rotation angle required to achieve a specified extension height of the modified scissor lift mechanism using an inverse kinematics equation in which extension height is an input variable;

(b) instructing the lead screw motor to rotate a required number of turns to reach the calculated lead screw rotation angle;

(c) monitoring whether the number of lead screw motor rotations indicates that the target vertical position has been reached; and (d) stopping the motor when the target vertical position, as determined by lead screw rotation angle, has been reached.

7. The method as recited in claim 6, further comprising producing simulated encoder pulses that represent unit vertical displacements of the distal portion of the modified scissor lift mechanism using a forward kinematics equation in which the rotation angle of the lead screw is an input variable.

8. The method as recited in claim 7, further comprising:

converting the simulated encoder pulses into current vertical position data indicating a current vertical position of the distal portion of the modified scissor lift mechanism;

pulsing an ultrasonic transducer array that is mounted on the distal portion of the modified scissor lift mechanism;

receiving ultrasound energy returned to the ultrasonic transducer array;

converting the received ultrasound energy into scan data; and storing the current vertical position data and the scan data in association in memory.

9. A lifting system comprising:

a lead screw in horizontal orientation;

a motor coupled to said lead screw for driving rotation of said lead screw;

a modified scissor lift mechanism coupled to said lead screw, a vertical position of a distal portion of said modified scissor lift mechanism being a nonlinear function of rotation of said lead screw;

an encoder for measuring each rotation of the lead screw through a predetermined angle into a respective rotation encoder pulse, and a computer system programmed to control said motor in accordance with a motion control algorithm comprising:

(a) calculating a lead screw rotation angle required to achieve a specified extension height of the modified scissor lift mechanism using an inverse kinematics equation in which extension height is input variable;

(b) instructing the lead screw motor to rotate a required number of turns to reach that the calculated lead screw rotation angle;

(c) monitoring whether the number of lead screw motor rotations indicates that the target vertical position has been reached; and (d) stopping the motor when the target vertical position, as determined by lead screw rotation angle, has been reached.

10. The system as recited in claim 9, further comprising a frame that supports said lead screw, said motor and said modified scissor lift mechanism, wherein said modified scissor lift mechanism comprises:

a first support block fixedly mounted to said frame;

a second support block that is supported by and slidable relative to said frame;

a first link having a proximal end pivotably coupled to said first support block; and a second link having a length twice that for the first link and a proximal end pivotably coupled to said second support block, said first and second links being pivotably coupled to each other at a midpoint of said second link, and wherein said lead screw is rotatably coupled to said first support block and threadably coupled to said second support block so that said second support block will move linearly relative to said first support block when said lead screw rotates.

11. The system as recited in claim 10, wherein said modified scissor lift mechanism further comprises a third link having a proximal end pivotably coupled to said second support block, wherein said second and third links are mutually parallel, and a payload platform pivotably coupled to distal ends of said second and third links.

12. The system as recited in claim 11, further comprising a tool attached to said payload platform.

13. The system as recited in claim 12, wherein said tool comprises an ultrasonic transducer array.

14. The system as recited in claim 13, further comprising a pulser/receiver in electrical communication with said ultrasonic transducer array, wherein said computer system is further programmed to control said pulser/receiver in accordance with a scanning algorithm comprising sending simulated encoder pulses to said pulser/receiver.

15. The system as recited in claim 11, wherein said modified scissor lift mechanism further comprises:
   first and second joints which respectively pivotably couple said proximal ends of said second and third links to said second support; and
   third and fourth joints which respectively pivotably couple said distal ends of said second and third links to said payload platform,
   wherein the axes of said first through fourth joints are located at respective vertices of a parallelogram.

16. The system as recited in claim 9, wherein said modified scissor lift mechanism has multiple stages.

17. A system comprising:
   a hollow composite structure comprising a spar web and first and second skins;
   a tractor vehicle disposed under said second skin, said tractor vehicle comprising a first frame, a plurality of wheels rotatably mounted to said first frame and in contact with said second skin, first and second magnet poles mounted on said first frame;
   a first trailer vehicle disposed above said second skin and on one side of said spar web, said first trailer vehicle comprising a second frame, a plurality of wheels rotatably mounted to said second frame and in contact with said second skin, a third magnet pole carried by said second frame and magnetically coupled to said first magnet pole through said second skin, a horizontal lead screw, a motor coupled to said lead screw for driving rotation of said lead screw, a modified scissor lift mechanism coupled to said lead screw, a payload platform pivotably coupled to a distal portion of said modified scissor lift mechanism, and a non-destructive inspection sensor mounted to said payload platform, wherein a vertical position of said distal portion of said modified scissor lift mechanism is a nonlinear function of rotation of said lead screw; and
   a second trailer vehicle disposed above said second skin and on another side of said spar web, said second trailer vehicle comprising a third frame, a plurality of wheels rotatably mounted to said third frame and in contact with said second skin, a fourth magnet pole magnetically coupled to said second magnet pole through said second skin.

18. The system as recited in claim 17, wherein said first trailer further comprises a fifth magnet pole and said second trailer vehicle further comprises a sixth magnet pole magnetically coupled to said fifth magnet pole through said spar web.

19. The system as recited in claim 17, wherein said modified scissor lift mechanism comprises:
   a first support block fixedly mounted to said second frame;
   a second support block that is supported by and slidable relative to said second frame; and
   a first link having a proximal end pivotably coupled to said first support block and a second link that is twice the length of the first link and having a proximal end pivotably coupled to said second support block, said first and second links being pivotably coupled to each other at the distal end of the first link and the midpoint of said second link,
   wherein said lead screw is rotatably coupled to said first support block and threadably coupled to said second support block so that said second support block will move linearly relative to said first support block when said lead screw rotates, and a vertical position of a distal end of said first link is a nonlinear function of rotation of said lead screw.

20. The system as recited in claim 17, wherein said modified scissor lift mechanism has multiple stages.

* * * * *